(12) United States Patent
Saunders et al.

(10) Patent No.: US 9,242,028 B2
(45) Date of Patent: Jan. 26, 2016

(54) MICROGEL PARTICLE

(75) Inventors: Brian Saunders, Cheshire (GB); Anthony John Freemont, Manchester (GB); Jennifer Saunders, Cheshire (GB)

(73) Assignee: Gelexir Healthcare Limited, Manchester (GB)

( * ) Notice: Subject to any disclaimer, the term of this patent is extended or adjusted under 35 U.S.C. 154(b) by 185 days.

(21) Appl. No.: 12/094,180

(22) PCT Filed: Nov. 23, 2006

(86) PCT No.: PCT/GB2006/004367
§ 371 (c)(1),
(2), (4) Date: May 19, 2008

(87) PCT Pub. No.: WO2007/060424
PCT Pub. Date: May 31, 2007

(65) Prior Publication Data
US 2008/0254133 A1    Oct. 16, 2008

(30) Foreign Application Priority Data
Nov. 25, 2005    (GB) .................................. 0523999.1

(51) Int. Cl.
*A61L 27/50*    (2006.01)
*A61L 27/16*    (2006.01)
*A61F 2/44*    (2006.01)

(52) U.S. Cl.
CPC ................. *A61L 27/50* (2013.01); *A61L 27/16* (2013.01); *A61F 2/441* (2013.01); *A61F 2/442* (2013.01); *A61F 2002/444* (2013.01); *Y10S 524/916* (2013.01)

(58) Field of Classification Search
CPC ................................................ A61F 2002/444
See application file for complete search history.

(56) References Cited

U.S. PATENT DOCUMENTS

| 5,192,326 | A | * | 3/1993 | Bao et al. ................... 623/17.12 |
| 6,544,503 | B1 | | 4/2003 | Vanderhoff et al. |
| 2001/0051834 | A1 | | 12/2001 | Frondoza et al. |
| 2002/0151981 | A1 | * | 10/2002 | Ferree ......................... 623/17.16 |
| 2004/0091540 | A1 | * | 5/2004 | Desrosiers et al. ........... 424/486 |
| 2004/0101518 | A1 | | 5/2004 | Vacanti et al. |

FOREIGN PATENT DOCUMENTS

| WO | 9210982 | 7/1992 |
| WO | 9524430 | 9/1995 |
| WO | 0247587 | 6/2002 |

(Continued)

OTHER PUBLICATIONS

BE Rodriguez, MS Wolfe, M Fryd. "Nonuniform Swelling of Alkali Swellable Microgels." Macromolecules 1994, vol. 27, pp. 6642-6641.*

(Continued)

*Primary Examiner* — Isaac Shomer
(74) *Attorney, Agent, or Firm* — Hema Vakharia-Rao; Nixon Peabody LLP

(57) ABSTRACT

The present invention relates to compositions comprising a pH-responsive microgel particle, wherein the particle is adapted to undergo a conformational change in response to a variation in pH. The compositions may be used as medicaments for treating a disease characterized by damaged or degenerated soft tissues (e.g. intervertebral discs).

31 Claims, 6 Drawing Sheets

(56) References Cited

FOREIGN PATENT DOCUMENTS

| WO | WO 0247587 A2 * | 6/2002 | |
|---|---|---|---|
| WO | 2004047690 | 6/2004 | |
| WO | WO 2004047690 A2 * | 6/2004 | ............... A61F 2/44 |
| WO | 2007060424 | 5/2007 | |

OTHER PUBLICATIONS

E Larraz, C Elvira, J San Roman. "Design and Properties of Novel Self-Curing Acrylic Formulations for Application in Intervertebral Disks Restoration." Biomacromolecules, vol. 6, 2005, pp. 2058-2066. Available Online May 3, 2005.*

BR Saunders, HM Crowther, B Vincent. "Poly[(methyl methacrylate)-co-(methacrylic acid)] Microgel Particles: Swelling Control Using pH, Cononsolvency, and Osmotic Deswelling." Macromolecules, vol. 30, 1997, pp. 482-487.*

GB Search Report, Application No. GB0523999.1, dated Apr. 7, 2006; 1 page.

International Search Report, Application No. PCT/GB06/004367, dated Oct. 16, 2007, as published Jul. 17, 2008; 6 pages.

Hiratani, et al. "The nature of backbone monomers determines the performance of imprinted soft contact lenses as timolol drug delivery systems," Biomaterials 25 (2004); 1105-1113.

Young, et al. "Introduction to Polymers." Chapman and Hall, 1997 (2nd ed.), Introduction, pp. 1-14.

Zhang, et al. "In vivo biocompatibility and mechanical study of novel bone-bioactive materials for prosthetic implantation," J. Biomed. Mater. Res. 46 (1999); 279-286.

* cited by examiner

Figure:1
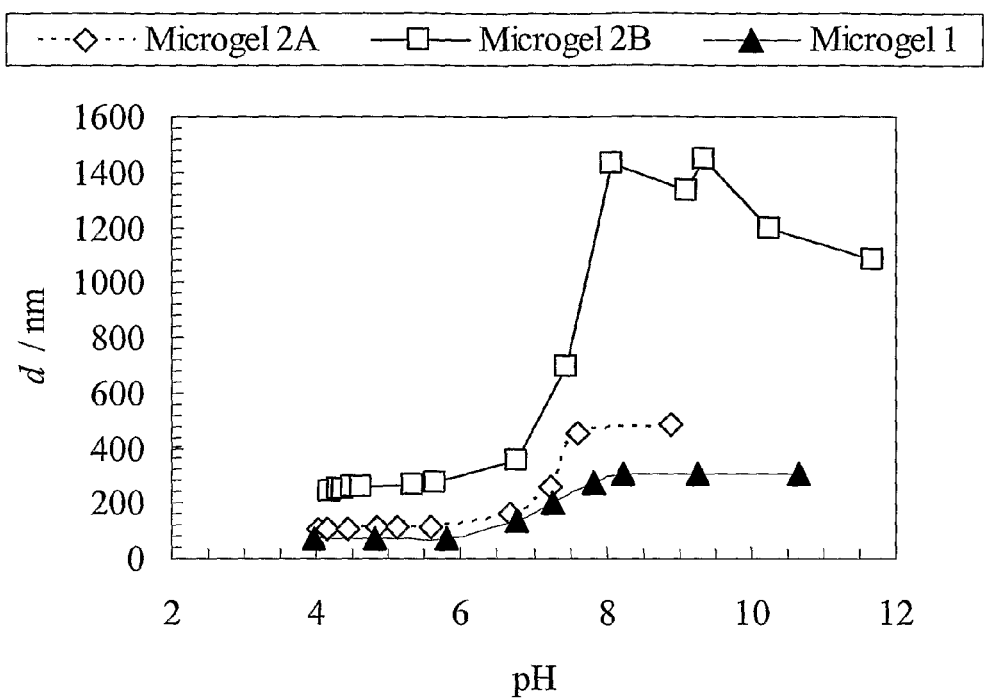
Figure:2
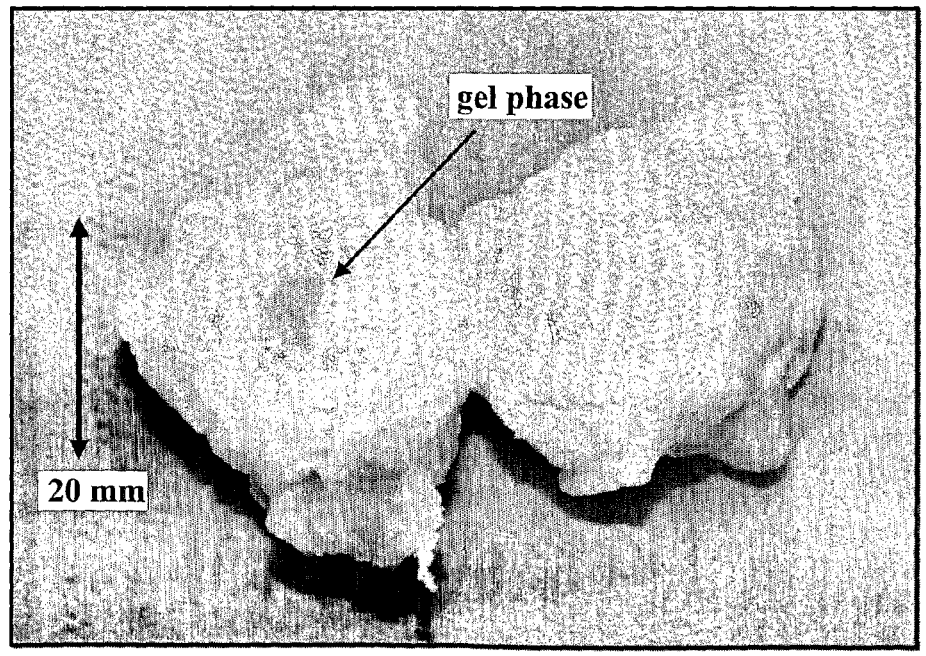

Figure:3
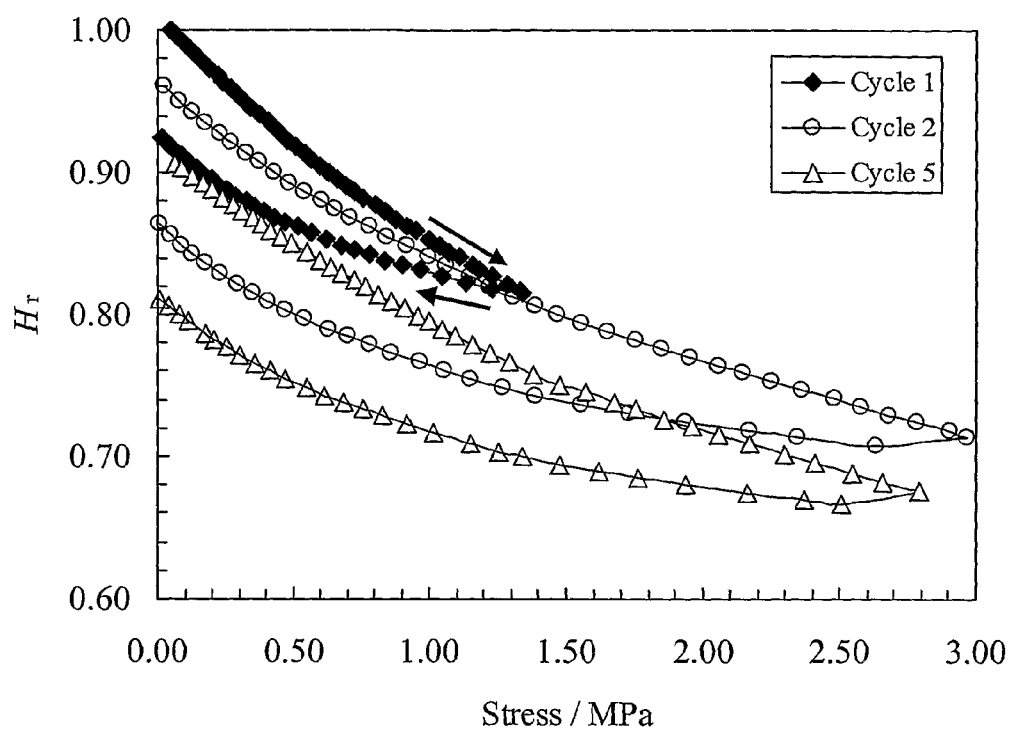

Figure: 4
(a)
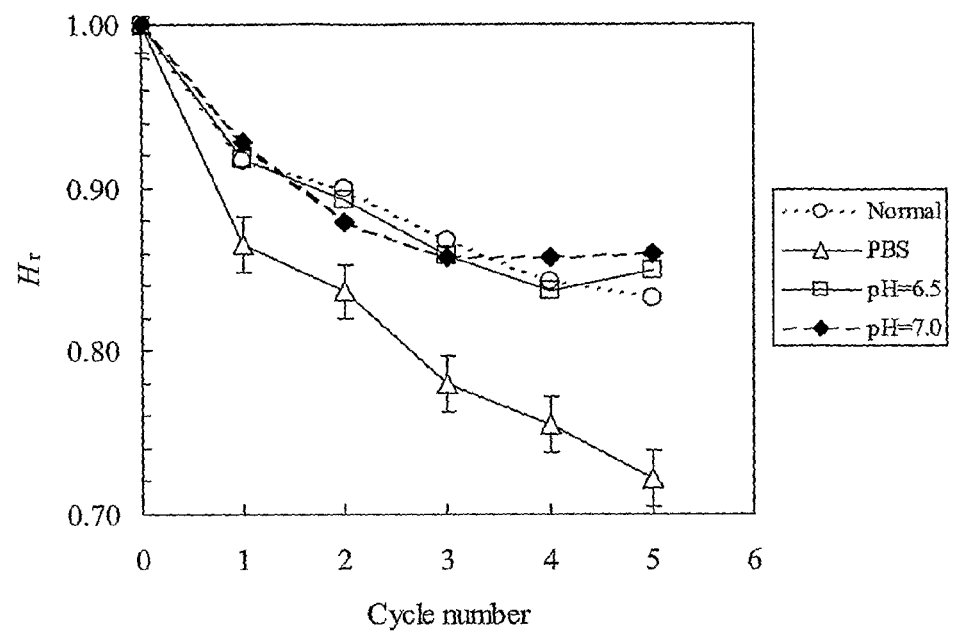
(b)
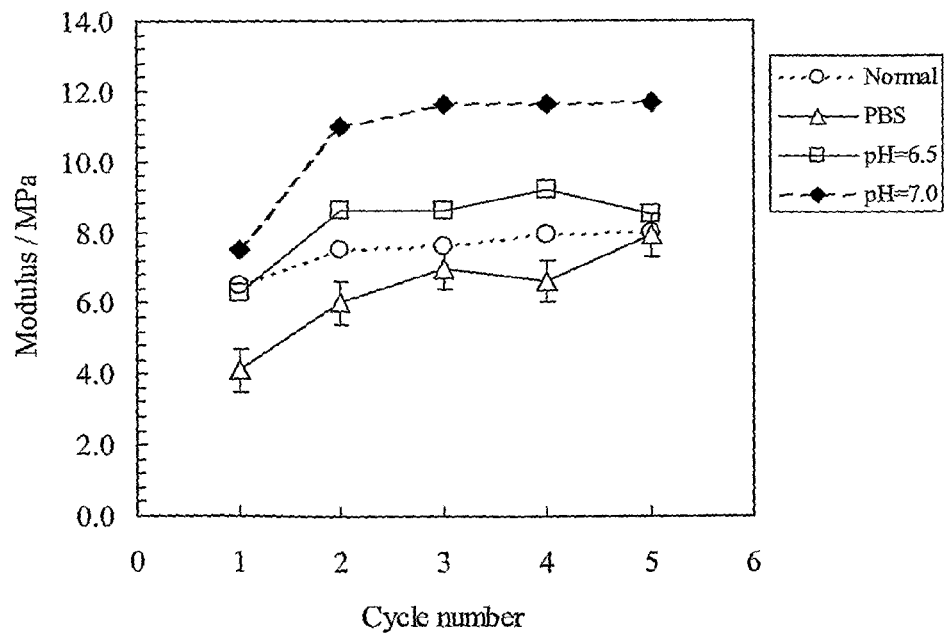

Figure:5
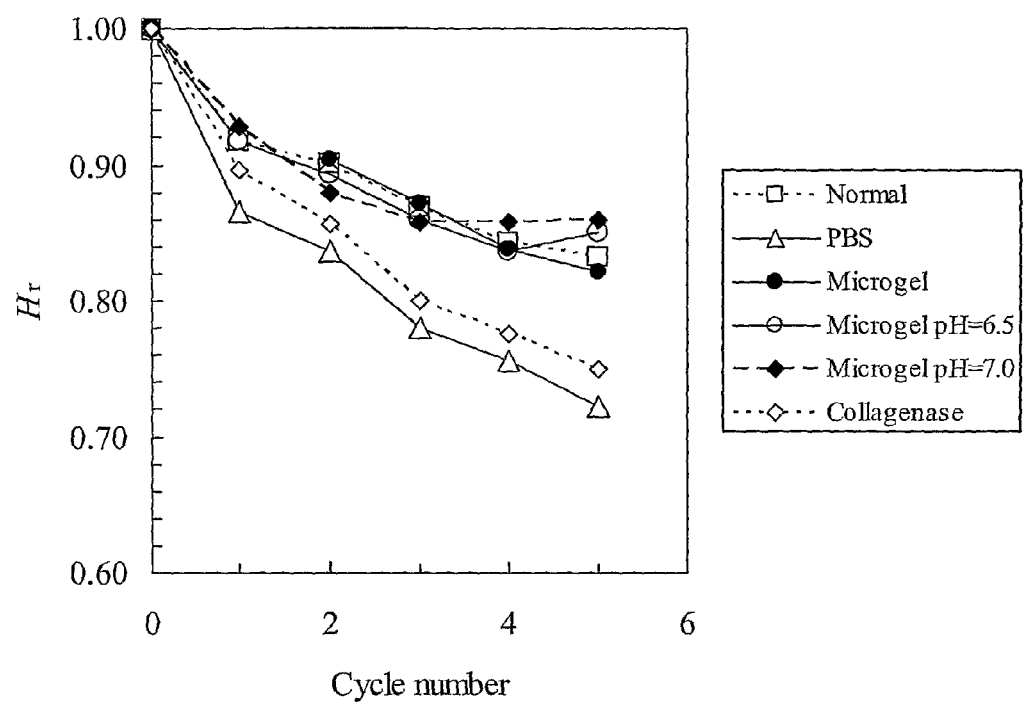

Figure: 6
Monomers used
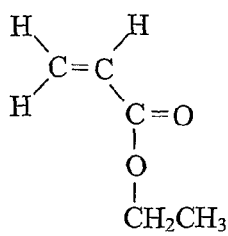
(EA)
Ethylacrylate
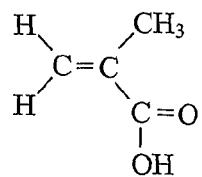
(MAA)
Methacrylic acid
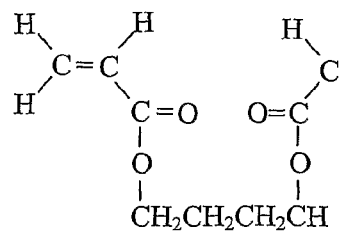
(BDDA)
1,4-butanediol diacrylate
Surfactant used
$CH_3(CH_2)_{11}OSO_3^-$
(SDS)
Sodium dodecylsulfate
Initiator used
$(NH_4^+)_2[S_2O_8^{2-}]$
(APS)
Ammonium persulfate
pH-buffer used
$K_2HPO_4$
di-potassium
hydrogenphosphate
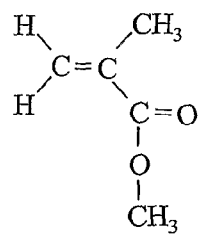
MMA
Methylmethacrylate
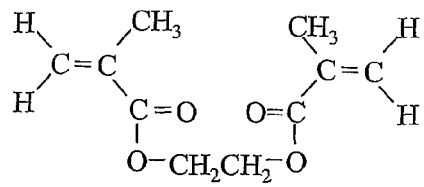
EGDMa
Ethyleneglycol dimethacrylate

Figure: 7
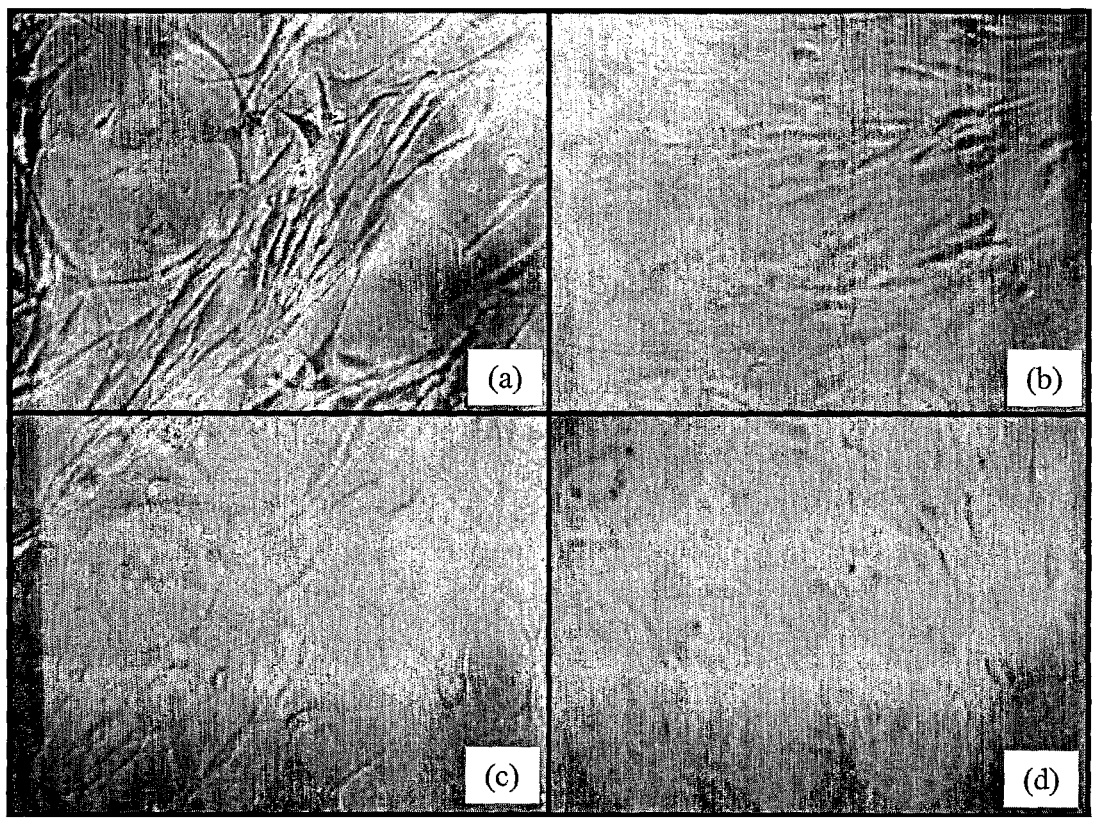

MICROGEL PARTICLE

This application is the National Phase of International Application PCT/GB2006/004367, filed Nov. 23, 2006, which designated the U.S. and that International Application was published under PCT Article 21(2) in English. This application also includes a claim of priority under 35 U.S.C. §119(a) and §365(b) to British patent application No. GB0523999.1, filed Nov. 25, 2005.

The present invention relates to microgel particles, and in particular, to microgel particles that are responsive to variations in pH, and the uses of such particles in methods for repairing soft tissue. The invention includes uses of the particles in methods of repairing damaged or inappropriately formed load-bearing tissue, for example, intervertebral disks.

The ability of soft tissue to adequately support biomechanical loads is essential to health and well-being, and the load-bearing requirements of soft tissues will depend on their location. The load-bearing requirements for tissue found in the articular joints (e.g., the ankle, knee and hip) and intervertebral discs (IVDs) are much greater than those for other soft tissues (e.g., human breast tissue). For example, the pressures experienced within human IVDs vary from about 0.5 MPa when sitting to about 2.3 MPa when lifting 20 kg.

The principle load-bearing tissue of the IVD is the disc-shaped nucleus pulposus (NP), i.e. the soft spongy material surrounded by the annular ring that makes up the centre of an intervertebral disc. The NP consists of chondrocytes (cartilage producing cells) within a matrix of collagen and proteoglycans. Articular cartilage, which is the tissue covering bony ends of articular joints, has a similar composition to that found in the NP. The proteoglycans have a high negative charge density and are responsible for the high NP swelling pressure. The NP is a natural ionic hydrogel and contains about 75% water in adults. The proteoglycan content decreases with age due to degeneration. This process results in the formation of "clefts" and a decreased ability to maintain disc height under load. The clefts are interconnected three-dimensional channels with millimeter-scale internal diameters.

Over 97% of all IVDs in the lower part of the spine are degenerated by the age of 50. This results in chronic back pain and greatly reduces the mobility in a significant proportion of people in this age group. Lower back pain is a major cause of sick leave in the UK.

Most current therapy of damaged IVDs is not targeted at the diseased disc per se, but rather at symptom relief. Surgical intervention is commonly used, which involves removal of the disc or spinal fusion. These strategies may relieve pain, but seriously alter spinal biomechanics, and often accelerate degeneration in adjacent discs. Hence, surgery is used as a last resort. Furthermore, such techniques represent major surgery with protracted hospital stay and significant morbidity in patients undergoing treatment.

A material science approach applied to the problem of repairing or preventing degradation of the IVD involves targeting the degenerated NP with molecules that may polymerise at the site of degeneration. One example includes the in situ polymerisation of poly(ethylene glycol) tetra-acrylate in the NP of the IVD. Another example includes injecting chitosan into the NP and allowing it to polymerise. Chitosan is a positively charged polysaccharide that is soluble in water at low pH. It undergoes a solution-to-gel transition when the pH is increased. It has therefore been contemplated that Chitosan may be injected as a low pH solution and then allowed to form a gel when it is exposed to a higher pH in vivo. The gel that forms in vivo is uncharged and forms a polymer network that occupies the whole volume of the injected solution. Hence, it becomes a macrogel through in situ polymerisation.

However a number of problems are associated with in situ polymerisation that make its use in a clinical setting at least questionable. A major problem with in situ polymerisation is that many polymerisations reactions are free-radical polymerisations that involve the use of toxic monomers and initiators. Such monomers and initiators can be highly unsuitable for use in vivo A further problem with in-situ polymerisation involving covalent bond formation is that the degree of cross-linking cannot be accurately controlled in-vivo. Furthermore, there is always the problem that there is a significant possibility of interfering reactions as well as unreacted material polymers etc.) that are potential candidates for causing cell damage.

An alternative approach is to use covalent bond formation within emulsion droplets to produce cross-linked polymer particles with diameters greater than 10 micrometers. However, a significant problem with this method is that it is limited to large particles and the particle size distribution will necessarily be broad. There are also limitations concerning the maximum volume fraction of polymer that can be achieved within the droplets due to the need to maintain a low viscosity of the dispersed phase.

It is therefore an object of the present invention to obviate or mitigate one or more of the problems of the prior art, whether identified herein or elsewhere, and to provide an improved method for repairing damaged and degenerated load-bearing tissue, using microgel particles.

It will be appreciated that a major challenge to improving techniques used for repairing load-bearing tissues such as IVDs, is to provide injectable materials that enable repair of the damaged and degenerated tissue. It should also be appreciated that a key criterion for such materials is that their mechanical properties suit those of the surrounding tissue.

The inventors have applied significant effort to investigate what materials may be used to repair soft tissues. One of their avenues of research was to investigate whether or not microgel particles, as described in more detail below, could be effectively used to repair the mechanical properties of load-bearing, soft tissue.

Microgel particles are known, and consist of microscopic cross-linked polymer colloid particles. Such microgel particles have been developed to act as intelligent drug release systems. The particles contain negatively charged carboxylate groups such that they are pH-responsive and able to swell at neutral pH. As the particles swell, they release their payload drug molecule. Microgel particles, which contain positive charged ammonium groups and are able to swell at neutral pH are also known.

However, to date, no-one has contemplated using such pH-responsive microgel particles for restoring the mechanical properties of damaged or degenerated load-bearing tissue, or soft tissue. The inventors hypothesised that a concentrated dispersion of pH-responsive microgel particles that contain high concentrations of carboxylic acid may provide an injectable fluid at a low pH (e.g. about pH 4.0) that would swell and thereby form a gel at a higher, physiological pH (i.e. about 7.4). The inventors reasoned that the swelling pressure within the swelling particles in the dispersion may be used to support loads similar to those experienced by intervertebral disc (IVD) tissue, and also in other load bearing tissues in the body. The swelling pressure originates from the high osmotic pressure that is generated within the particle interior as a consequence of ionisation of the microgel network at physiological pH. In the case of anionic carboxylic acid-containing microgel particles, this occurs due to deprotonation of carboxylic acid groups.

To their surprise the inventors were able to establish that such pH responsive microgels were very suitable for repairing soft tissues in vivo and, as discussed in more detail below, represent significant improvements over prior art techniques (e.g. in situ polymerisation based methods).

Hence, according to a first aspect of the present invention, there is provided use of a composition comprising a pH-responsive microgel particle, wherein the particle is adapted to undergo a conformational change in response to a variation in pH, for the manufacture of a medicament for treating a disease characterised by damaged or degenerated soft tissue.

The invention is based on the work illustrated in the Example. As described in the Example and as shown in FIG. 6, the inventors prepared a dispersion of pH-responsive microgel particles containing ethylacrylate, methacrylic acid and butanediol diacrylate co-monomer units. The dispersion was characterised using photon correlation spectroscopy (PCS) and scanning electron microscopy (SEM). The latter technique showed that they had an average size of about 65 nm and low polydispersity (coefficient of variation of about 11%). The PCS data are shown in FIG. 1, and the inventors observed that the diameter of the particles in the dispersion were dependent on the pH to which they were exposed. In use, the dispersion was maintained at a pH of about 4.0, and then injected into degenerated bovine IVDs (as shown in FIG. 2). The bovine IVDs were subjected to controlled degeneration using collagenase treatment. It will be appreciated that bovine IVDs are an established animal model for human IVDs.

The IVDs were then exposed to basic (alkali) conditions (which increased the pH towards physiological condition about pH 6.6 or preferably about pH 7.0), which caused the microgel particles in the dispersion to swell and form a gel as shown in FIG. 2. The IVDs were examined and, to their surprise, the inventors noticed that microgels according to the invention significantly improved the structure of the IVD and reduced degeneration. (The compression data as shown in the FIGS. 4 and 5 clearly illustrate that injection of the fluid microgel dispersion, which then gels and restores the mechanical properties of degenerated IVDs). The inventors believe that this novel approach using pH responsive microgel particles and dispersions thereof, would be applicable to any soft tissue, such as the tissue below the skin and articular cartilage.

The inventors have demonstrated a completely new method for using microgel particles as biomaterials. They have demonstrated for the first time that a composition comprising at least one, and preferably, a plurality of pH-responsive microgel particles, may be used in the manufacture of a medicament, which may be effectively used to repair or restore damaged or degenerated soft tissue as defined in the first aspect of the invention. Furthermore, the medicament of the first aspect may be used in a method to treat individuals suffering from a disease characterised by damaged or degenerated soft tissue.

Hence, according to a second aspect, there is provided a method of treating a subject suffering from a condition characterised by damaged or degenerated soft tissue, the method comprising administering to a subject in need of such treatment, a therapeutically effective amount of a composition comprising a pH-responsive microgel particle, wherein the particle is adapted to undergo a conformational change in response to a variation in pH.

Advantageously, the composition used in the method according to the second aspect, or the medicament manufactured in the first aspect may be very simply administered into the tissue being treated, for example by injection. This is therefore a minimally-invasive treatment. Hence, it will be appreciated that use of the composition to treat diseases characterised by damaged or degenerated soft tissue according to the invention is a much better solution than the far more invasive surgical methods currently used. Treatment is much quicker, and recovery time for the subject being treated is greatly reduced.

By the term "microgel particle", we mean a particle, which comprises a plurality of cross-linked co-monomers, which have formed a polymer network throughout each particle as a result of a polymerisation reaction. It should be appreciated that such a polymerisation will have been conducted during the preparation of a particle according to the invention and does not occur in situ. The microgel particle is preferably a cross-linked polymer particle that undergoes a conformation change and forms a gel (or microgel) in a 'good' solvent or in response to pH change. This may be referred to as a pH-triggered macrogelation step, in which the gelation takes place in situ in the tissue being treated. A good solvent is one, which causes the polymer network that forms the particle to expand. For a good solvent, the Flory-Huggins interaction parameter for the solvent-polymer system is preferably less than 0.5.

The microgel particle itself may be considered as being one macromolecule (i.e. the cross-linked polymer) comprising a molar mass of between about $10^6$ and $10^{10}$ Da. (e.g. between $10^6$ and $10^9$ Da). However, the individual co-monomers that were used during the preparation of the microgel particles may comprise a molar mass of between about 5 Da and 5,000 Da, more preferably, between about 10 Da and 1,000 Da, even more preferably, between about 50 Da and 500 Da, and most preferably, between about 75 Da and 400 Da. In a most preferred embodiment, the co-monomers used in the polymerisation reaction comprise a molar mass of about 100 Da and 300 Da.

Preferably, the microgel particle comprises water as the major dispersion medium for the cross-linked polymers. The water content may be quite variable, and increases with pH and decreasing salt concentration of the medium (i.e. ionic strength). Hence, the water content of the particle will depend on whether it is measured before or after administration to the subject, i.e. before or after exposure to the change in pH.

It is preferred that the composition comprises a plurality of pH responsive microgel particles, and preferably, a dispersion thereof. The dispersion is preferably adapted to form a particulate gel in response to the variation in pH. Hence, the individual particles are preferably adapted to swell to such an extent that most of the fluid is contained within the swollen particles, and they press against each other to form a macroscopic gel. In this swollen state, the particles are effectively trapped in position due to the inability to move past neighbouring particles. A microgel particle may also be referred to as a "gel-microparticle".

By the term "pH-responsive", we mean the microgel particle is operable to undergo the conformational change when exposed to a change (i.e. either an increase or a decrease) in pH.

Preferably, the particle comprises pH-responsive means, which is responsive to the variation in pH so as to modulate the conformation of the particle. In one embodiment, the pH responsive means may comprise a positively charged species or functional group. In this embodiment, the pH responsive means is basic, and may have a $pK_b$ between about 2.0 to 9.0, more preferably between about 4.5 to 7.5, even more preferably between about 5.0 to 7.0 and most preferably, between about 5.5 to 6.5.

However, in a preferred embodiment, the pH responsive means comprises a negatively charged species or functional group, and is acidic. In this embodiment, it is preferred that the $pK_a$ of the pH responsive means is between 1.0 to 12.0, more preferably between 3.0 to 10.0, even more preferably, between 5.0 to 8.0, and most preferably, between 6.0 to 7.0.

Preferably, the composition comprises a plurality of microgel particles. It should be appreciated that the plurality of particles may consist of more than one of the same type of microgel particle, ie. in which the same co-monomers are used to form the same cross-linked polymer. However, it is also envisaged that the plurality of particles may consist of at least two (or more) types of different particle, i.e. in which different co-monomers are used to form different cross-linked polymers.

Preferably, the pH of the composition prior to administration is less than the pH of the tissue being treated, which is preferably at physiological pH. Therefore, the pH of the microgel particle prior to exposure to the variation in pH is preferably between about 4.0-7.0, more preferably, between about 4.5-6.0, and most preferably, between about 5.0-6.0. The composition may comprise a colloid dispersion of the microgel particles. Preferably, prior to exposure to the variation in pH, the composition is substantially fluid. This is a result of the particles in the composition adopting a collapsed configuration. Hence, prior to exposure to the variation in pH, it is preferred that the microgel particle adopts a substantially collapsed configuration or conformation.

By the term "collapsed configuration", we mean the particle is substantially reduced in size having a smaller average diameter before exposure to the pH variation compared to the average diameter of the particle after the pH variation. The limit of the collapsed form is when the particle contains virtually no water when injected. For example, prior to administration of the composition (i.e. when it is in the injectable state), the water content in the particle is preferably low due to the low pH at which the particles are maintained. Hence, the microgel particle preferably comprises less than about 70% (w/w) water, more preferably, less than about 50% (w/w) water, preferably, less than about 30% (w/w) water, and even more preferably, less than about 20% (w/w) water, and most preferably, less than about 10% (w/w) water prior to administration of the composition (i.e. before exposure to the pH change). However, in a preferred embodiment (as in the example given), the particles comprise a minor proportion of water (less than about 40% w/w) prior to administration. It will be appreciated that this water content is with reference to the water within the particle. The particles may be suspended in a medium that is substantially aqueous.

It will be appreciated that the diameter of the particles will depend upon the water content thereof which is in turn dependent upon the pH. The diameter of the microgel particle prior to exposure to the variation in pH (prior to administration) is preferably less than about 100 μm, more preferably, less than about 50 μm, and even more preferably, less than about 20 μm. However, in a preferred embodiment, it is preferred that the diameter of the microgel particle prior to exposure to the variation in pH is less than about 10 μm, more preferably, less than about 5 μm, and even more preferably less than about 1 μm. Most preferred particles are on the nanometer scale, i.e. the diameter of the microgel particle prior to exposure to the variation in pH is preferably between about 1 nm-1000 nm, more preferably, between about 10 nm-750 nm, even more preferably, between about 20-500 nm, and most preferably, between about 50-100 nm in diameter.

In use the composition is administered to a subject such that it is exposed to the variation in pH. It will be appreciated that the pH of the composition and hence microgel particle after administration to the subject will depend on the specific tissue being treated. The pH of the microgel particle after exposure to the variation in pH may be between 5.5-8.0, more preferably, between about 6.0-7.8, and most preferably, between about 6.0-7.5. Preferably, following administration of the composition, the pH of the particle is preferably at a physiological pH, i.e. approximately, pH 7.4. However, some damaged tissues to which the composition is administered may have a different pH to 'normal' physiological pH. For example, the pH of intervertebral disks (IVD) is about 6.6. Hence, the pH of the particle after administration to the subject being treated is preferably between about 5.0-8.0, and more preferably, between about 5.5-7.8, and most preferably, between about 6.0-7.5, and most preferably, about 6.6.

Hence, it will be appreciated that after exposure of the particle to the variation in pH, the microgel particle undergoes the conformational change. By the term "conformational change", we mean the average diameter of the microgel particle changes in response to the variation in pH. The average diameter of the particle may increase or decrease in response to the variation in pH. This will depend on the chemical composition of the polymer in the microgel particle. It will be appreciated that the variation in pH may comprise either an increase or decrease in pH, which causes the conformational change in the particle.

In one embodiment, the diameter of the at least one microgel particle may decrease or adopt a collapsed configuration, in response to a variation in pH, for example, a decrease in pH. However, it is preferred that the diameter of the microgel particle increases or adopts a substantially swollen configuration or conformation in response to the variation in pH, for example, an increase in pH. By the term "swollen configuration", we mean the particle is substantially enlarged, and therefore has a greater average diameter after exposure to the pH change (after administration), as compared to the diameter of the particle before the pH variation, i.e. before administration of the composition to the subject.

It will be appreciated that this swelling is caused by a flow of water into the particle. Hence, following administration, i.e. when the particle is in the swollen state (for example, as shown in FIG. 1), the microgel particle preferably comprises at least about 70% (w/w) water, more preferably, at least about 85% (w/w) water, preferably, at least about 90% (w/w) water, even more preferably, at least about 95% (w/w) water, and most preferably, at least about 99% (w/w) water. It will be appreciated that the amount of water in the particle depends on pH. Hence, at low pH (e.g. about pH 2.0), the water content may be less than about 5% (w/w).

Suitably, the average diameter of the microgel particle after exposure to the variation in pH, is adapted to increase by at least 50%, more suitably, by at least 200%, more suitably by at least 300%, even more suitably, by at least 400%. It is preferred that the average diameter of the microgel particle after exposure to the variation in pH, is adapted to increase by at least 600%, more suitably by at least 800%, even more suitably, by at least 1000%, and still more suitably by at least 1200%.

For example, the diameter of the microgel particle after exposure to the variation in pH is preferably between about 1 nm-1000 nm, more preferably, between about 50 nm-750 nm, even more preferably, between about 100-600 mm, and most preferably, between about 200-400 nm in diameter.

As a result of this swelling effect of the at least one particle when exposed to the variation in pH (i.e. the increase in pH), preferably, the composition is adapted to transform from a substantially fluid conformation to a gel like structure. Hence, a key effect of the pH change is that the dispersion of particles has a low viscosity at the pH of administration, and this viscosity increases greatly once the pH approaches physiological pH, and a load-bearing gel is formed. It will be appreciated that the microgel particles are themselves a polymer network, i.e. they are gelled microparticles. However, when they are in a concentrated dispersion (e.g, following administration to a subject), they swell in response to the pH increase and the dispersion itself transforms from a fluid to a gel. The resultant gel may be referred to as a gelled, microgel dispersion. The gelation of the dispersion results from lack of space between particles. Accordingly, it is preferred that the conformational change of the particles in the composition comprises a gelation step, which preferably occurs in situ in the tissue being treated. Advantageously, it will be appreciated that it is when the composition is in this gel structure, that it can confer load-bearing effects on the target tissue, thereby treating the disease condition.

The inventors believe that the microgel particles and hence, microgels produced thereby, have a number of structural features that significantly favour their use as load-bearing materials, and particularly injectable load-bearing materials. Firstly, it is preferred that the microgel particle, and hence, gel, which results upon exposure to the variation in pH, is substantially anionic. Because most proteins bear a net negative charge at physiological pH (i.e. they are anionic), their adsorption onto such anionic microgels produced by the composition when exposed to the pH variation is opposed electrostatically. Secondly, it is preferred that the microgel particles comprise at least about 90% (w/w) water, and more preferably, at least 99% (w/w) water when in the fully swollen state, and will therefore have interfacial tensions approaching zero. Hence, while the inventors do not wish to be bound by any hypothesis, they believe that both of these factors minimise any potentially cytotoxic effects of the composition when administered to the subject being treated. This is a considerable advantage for the medicament according to the first aspect or the method of the second aspect.

Preferably, the swollen particles comprise a substantially high concentration of mobile ions. These ions originate from counter-ions that neutralise the carboxylic acid groups at physiological pH. The ions may comprise either Group I alkali metal ions or Group II alkaline earth metal ions. However, it is preferred that the ions are $Na^+$ or $K^+$ ions, which are present in high concentrations in the body. However, it will be appreciated that other cations present in the body could also fulfil this role. The inventors believe that the high concentration of mobile ions within the swollen particles at pH values above the $pK_a$ value of the microgel particles, results in high swelling pressures.

Advantageously, the swollen particles following exposure to the pH change, are too large to migrate away from the site of administration, for example, via permeation through cell walls and non-degenerated tissue. Hence, the particles are confined to the site of administration, which greatly maximises their load-bearing ability. This is another significant advantage of the composition according to the invention.

Hence, from the foregoing, it will be appreciated that a key component of the present invention is the nature and composition of the microgel particle used in the composition used to manufacture the medicament according to the first aspect, or used in the method of the second aspect. It will be appreciated that the pH-responsive microgel particles used according to the invention may be prepared using any of the commonly available polymerisation techniques. For example, the particles may be prepared using free radical emulsion polymerisation (Rodriquez, B. E., Wolfe, M. S and Fryd, M. Macromolecules, 27, 6642, 1994).

Preferably, the particle comprises cross-linked polymer chains resulting from a polymerisation reaction between a plurality of monomers or co-monomers. It is preferred that the particles used in accordance with the invention are cross-linked prior to administration to the subject being treated, and advantageously, no further cross-linking occurs after administration. However, preferably, the particle does not contain any polymer prior to the cross-linking step.

By the term "co-monomer", we mean a monomer, which co-polymerises with at least one other monomer in a polymerisation reaction. The co-monomers are contacted with each other under suitable conditions, such that they co-polymerise to form copolymer chains (referred to as polymer chains), preferably in the presence of an initiator. The copolymer chains precipitate out of solution to form nuclei particles. Co-monomers add to these growing nuclei particles to form larger particles by free-radical chain polymerisation. The process continues and the polymer particles containing co-monomer chains (which are cross-linked) get larger. When the process is complete there is one large polymer chain that comprises the microgel particle according to the invention.

Hence, the microgel particle comprises a plurality of cross-linked co-monomer units that form a polymer network that occupies the whole particle. This occurs as the result of the polymerisation reaction between the various co-monomers. Suitable monomers will be known to the skilled technician, and preferred monomers are described herein below.

Other ways of forming microgels according to the invention may involve the following polymerisation methods:

(A) The microgel particles may be prepared using suspension polymerisation. This would result in micrometer sized particles being produced. In this embodiment, an organic-soluble initiator may be used (for example, azoisobutyronitrile).

(B) Another method for the preparation of microgel particles may involve inverse microemulsion polymerisation. This would result in nanometer sized particles being produced. An organic soluble initiator may be used. An organic solvent (e.g., toluene) is dispersed in water as a microemulsion using a surfactant such as AOT (sodium di-2-ethylhexylsulfosuccinate).

The Example provides details of preferred methods for preparing the particles used in the invention.

In a preferred embodiment of the invention, the particles are prepared by providing a co-monomer mixture comprising ethylacrylate (EA), methacrylic acid (MAA), and 1,4-butanediol diacrylate (BDDA) to form the polymer: poly(EA/MAA/BDDA). Preferably, the mixture comprises a suitable surfactant, and preferably, a suitable buffer. Once the mixture is prepared, the polymerisation reaction is then initiated. It should be appreciated that an initiator does not have to be used, for example, if heat or irradiation with radical-producing radiation is used. An example would be the use of gamma-irradiation, which would initiate the polymerisation reaction. However, it preferred that polymerisation is triggered using an initiator, or initiating agent.

In another preferred embodiment of the invention, the particles are prepared by providing a co-monomer mixture comprising methylmethacrylate (MMA), methacrylic acid (MAA), and ethyleneglycol dimethaacrylate (EGDMa) to form the polymer: poly(MMA/MAA/EGDMa). Preferably, the mixture comprises a suitable surfactant, and preferably, a suitable buffer. Once the mixture is prepared, the polymerisation reaction is initiated. The components for poly(MMA/MAA/EGDMa) are already used in biomedical devices such as bone cement[Zhang et al., Journal of Biomaterials Research, 46, 279, 1999] and contact lenses[Hiratani et al., Biomaterials, 25, 1105, 2994]. Therefore, such microgels are particularly useful because they are known to be biocompatible with human tissue.

It is also envisaged that the microgel particle may comprise a so-called multi-layer particle, which comprises more than one layer of cross-linked polymer as defined herein. Hence, the particle may comprise an inner core made using suitable comonomers, and then one or more outer shell or layer is preferably, polymerised onto the inner core using those monomers or other types which could be grafted onto them using other free-radical or non-free-radical polymerisation methods. This process may be repeated numerous times to increase the number of layers (i.e. shells) on the particle. It would be possible to use another polymer as the inner core, for example, a biodegradable polymer such as polylactic acid, polyglycolic acid, polylactone, copolymer of lactic acid and glycolic acid or combinations thereof, and then to use those particles as a seed to grow an outer shell comprising pH-responsive microgel cross-linked polymer as defined herein below.

The free radical method of preparing the particle has a number of advantages over other polymerisation reactions, such as chemical (non-free radical) polymerisation. For example, the same chemistry can be used for a wide variety of monomers. Furthermore, the particle size can be varied over a large range. Moreover, the size distribution of the particles is narrow. Furthermore, this technique may be used to prepare multi-layer particles, i.e., core-shell particles.

It will be appreciated that a key component of the microgel particle is a pH-responsive co-monomer, and means for cross-linking the co-polymers. Hence, it is preferred that the microgel particle comprises a pH-responsive co-monomer and a functional cross-linking co-monomer. Hence, it is preferred that the microgel particle comprises a co-polymerised polymer particle, which may be defined by the following formula I:—

Poly(P-co-X)  Formula I wherein, P is a pH-responsive co-monomer; and X is a functional cross-linking co-monomer. For the sake of clarity, the nomenclature used herein in respect of the polymer which constitutes the microgel particle is taken from R. J. Young and P. A. Lovell, Introduction to Polymers, $2^{nd}$ Edition, Chapman and Hall, 1997. (pp. 8-10), which will be known to the skilled technician.

The term "poly" indicates that the particle is a co-polymer.

By the term "pH-responsive co-monomer", we mean a monomer that contains at least one functional group that is either acidic or basic and, when incorporated into the co-polymer chain or network, causes a significant conformational change in response to a variation in pH. It will be appreciated that the pH responsive means defined herein comprises the pH responsive co-monomer.

Preferably, the pH-responsive co-monomer is incorporated into the co-polymer at a significant level, for example at greater than 5 mol %. In embodiments where the pH-responsive co-monomer is acidic, then the $pK_a$ of the acidic groups may be between 1.0 and 12.0. However, preferably, the $pK_a$ is between 6.0-7.0. In embodiments where the pH responsive co-monomer is basic, then the $pK_b$ of the basic groups may be between 2.0 and 12.0. However, preferably, the $pK_b$ is between 5.5-6.5.

By the term "functional cross-linking co-monomer", we mean a monomer that contains two or more double bonds that are susceptible to chain addition through free-radical polymerisation.

The pH responsive co-monomer, P, may comprise a plurality of basic repeat units. However, preferably, the pH responsive co-monomer, P, comprises a plurality of acidic repeat units.

The pH-responsive co-monomer, P, may be defined by the following formula II:—

$$R^1R^2C=CR^3R^4 \qquad \text{Formula II}$$

wherein, (a) $R^1$, $R^2$ and $R^3$ may be independently selected from a group consisting of H; $CH_3$; a linear or branched alkyl group; a dialkyl group; or a N-alkyl group;

and wherein (b), $R^4$ may be independently selected from a group consisting of:—
(i) a carboxylic acid; COOH or $R^5$—COOH, wherein $R^5$ comprises $CH_2$, a linear or branched methylene (—$CH_2$—) group; a dialkyl group; a $C_6H_4$ group or substituted $C_6H_3R^6$, wherein $R^6$ comprises a substituent, such as $CH_3$; a halogen; or an amide group; or other di- or tri-substituted phenyl groups comprising more than one of these substituents;
(ii) an aminoacrylate of the form —C(=O)—$OR^7$, wherein $R^7$ is —$R^8NR^9R^{10}$, wherein $R^8$ may be —$CH_2$—, —$CH_2CH_2$— or a linear, or branched, methylene chain up to 10 chains in length, or —$C_6H_4$—, $C_6H_3R^{11}$, wherein $R^{11}$ comprises substituents such as $CH_3$, a halogen or an amide group or other di- or tri-substituted phenyl groups containing more than one of these substituents, and wherein $R^9$ and $R^{10}$ may be independently selected from the following H; $CH_3$; $CH_2CH_3$; a linear or branched alkyl group; a dialkyl group; or a N-alkyl group, for example of up to 10 C units;
(iii) —C(=O)—NH—C(CH_3)_2—CH_2—SO_3H;
(iv) an ester group that degrades to a carboxylic acid by hydrolysis, i.e., —O—C(=O)—$R^{11}$, wherein $R^{11}$ is —$C(CH_3)_3$, or a linear or branched alkyl group of up to 20 C units; and
(v) an amine of the form, —$NR^{12}R^{13}$, wherein $R^{12}$ and $R^{13}$ may be independently selected from a group consisting of H; $CH_3$; a linear or branched alkyl group; a dialkyl group; or a N-alkyl group of up to 20 C units.

However, it is especially preferred that P comprises a pH-responsive co-monomer, for example, a substituted acrylic acid. Hence, P may comprise acrylic acid. Hence, preferably, P comprises methacrylic acid (MAA).

Preferably, the functional cross-linking co-monomer, X, comprises a plurality of cross-linked polymer chains. The cross-linking co-monomer, X, may be defined by the following formula III:—

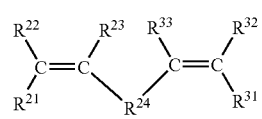

Formula III wherein, (a) $R^{21}$, $R^{22}$, $R^{23}$, $R^{31}$, $R^{32}$ and $R^{33}$ may be independently selected from a group consisting of H; $CH_3$; a linear or branched alkyl group; a dialkyl group; or a N-alkyl group of up to 10 C units; and wherein (b) $R^{24}$ may be independently selected from a group consisting of:—
- (i) $-C(=O)-O-R^{34}-O-C(=O)-$, wherein $R^{34}$ may comprise $-CH_2-$, $-CH_2CH_2-$ or a linear or branched alkyl group, such as a methylene chain, which may be up to 20 C chains in length; or $-C_6H_4-$; or $C_6H_3R^{35}$, wherein $R^{35}$ comprises substituents such alkyl, for example, $CH_3$; a halogen group; or an amide group; or other di- or tri-substituted phenyl groups containing more than one of these substitutents;
- (ii) $-C(=O)-O-R^{36}-C(=O)-$, wherein $R^{36}$ may be $-(CH_2CH_2O)$, wherein n may be from 1 to 30;
- (iii) $-C(=O)-O-R^{37}R^{38}R^{37}-$, wherein $R^{37}$ may comprise degradable ester linkages, for example lactone, $-[(CH_2)_5C(=O)-O]_m-$, lactide, $-[CH(CH_3)C(=O)-O]_m-$, glycolide, $-[CH_2C(=O)-O]_m-$, wherein m may be from 1 to 50, and wherein $R^{38}$ may be $-(CH_2CH_2O)_n-$, wherein n may be from 1 to 30;
- (iv) $-C(=O)-O-R^{39}-$, wherein $R^{39}$ may comprise degradable ester linkages, for example lactone, $[(CH_2)_5 C(=O)-O]_n-$, lactide, $[CH(CH_3)C(=O)-O]_m-$, glycolide, $[CH_2C(=O)-O]_m-$, wherein m is between 1 to 100;
- (v) allylacrylates, for example $-C(=O)-O-R^{40}-$, wherein $R^{40}$ may be $-CH_2-$, $-CH_2CH_2-$ or a linear, or branched, methylene chain up to 20 C chains in length, or $-C_6H_4-$, $C_6H_3R^{41}$, wherein $R^{41}$ may comprise substituents, such as alkyl, $CH_3$, a halogen or an amide group or other di- or tri-substituted phenyl groups containing more than one of these substitutents;
- (vi) vinylbenzenes, for example $C_6H_4$ or $C_6H_3R^{42}$ wherein $R^{42}$ comprises substituents, such as alkyl; $CH_3$; a halogen or an amide group (see (iii) above); or other substituted phenyl groups containing more than one of these substitutents;
- (vii) acrylamides, for example $C(=O)-NR^{43}-R^{44}-NR^{45}C(=O)-$, wherein $R^{43}$ and $R^{44}$ may be independently selected from a group consisting of H; $CH_3$; a linear or branched alkyl group; a dialkyl group; a N-alkylgroup, of up to 10 C units; and wherein $R^{44}$ may comprise $-CH_2-$, $-CH_2CH_2-$ or a linear, or branched, methylene chain up to 20 C chains in length; or $-C_6H_4-$, $C_6H_3R^{41}$ wherein $R^{41}$ comprises substituents, such as alkyl; $CH_3$; a halogen or an amide group or other di- or tri-substituted phenyl groups containing more than one of these substitutents;
- (viii) trifunctional cross-linking monomers, wherein $R^{24}$ comprises any of the groups listed in (b), as well as $R^{21}R^{22}=CR^{23}$, where $R^{21}$, $R^{22}$ and $R^{23}$ are described in (a);
- (ix) tetrafunctional cross-linking monomers, wherein $R^{24}$ comprises any of the groups listed in (b), as well as $R^{21}R^{22}C=CR^{23}$ and $R^{31}R^{32}C=CR^{33}$, wherein $R^{21}$, $R^{22}$, $R^{23}$, $R^{31}$, $R^{32}$ and $R^{33}$ are described in (a); and
- (x) wherein $R^{24}$ may contain any combination of the groups listed in (b).

However, it is preferred that X comprises a functional preferably, a di- a higher functionality) cross-linking co-monomer, for example, a substituted functional acrylate. Hence, X may comprise allylmethacrylate or divinylbenzene. Hence, X may comprise butanediol diacrylate (BDDA). However, preferably, X comprises ethyleneglycol dimethacrylate (EGDMa).

The functional cross-linking co-monomer may have other groups in between the terminal vinyl groups, for example poly(ethyleneglycol)dimethacrylate. Alternatively, the cross-links may be formed by reactions between co-monomers after particle formation.

It is preferred that the microgel particle comprises a hydrophobic co-monomer. Hence, it is preferred that the microgel particle comprises a co-polymerised polymer particle, which may be defined by the following formula IV:—

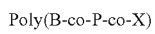

Formula IV wherein, P, and X are as defined in Formula I, and wherein B is a hydrophobic co-monomer.

By the term "hydrophobic co-monomer", we mean a monomer whose respective homopolymer is substantially insoluble in water.

Preferably, the hydrophobic co-monomer, B, comprises a plurality of hydrophobic repeat units. The hydrophobic co-monomer, B, may be defined by the following formula V:—

Formula V wherein, (a) $R^{51}$ and $R^{52}$ may be independently selected from a group consisting of H; $CH_3$; a linear or branched alkyl group; a dialkyl group; an N-alkyl group;

and wherein, (b) $R^{53}$ and $R^{54}$ may be independently selected a group consisting of:—
- (i): H; $CH_3$; or a linear or branched alkyl group;
- (ii) an ester of the form $-C(=O)-OR^{55}$, wherein $R^{55}$ comprises $CH_3$; a linear or branched alkyl group; a dialkyl group; or a N-alkylgroup;
- (iii) an amide of the form $CONR^{56}R^{57}$, wherein $R^{56}$ and $R^{57}$ may be independently selected from H; $CH_3$; a linear or branched alkyl group; a dialkyl group; or an N-alkyl group;
- (iv) $C_6H_5$ or $C_6H_4R^{58}$, wherein $R^{58}$ may comprise a substituent group, for example, $CH_3$; a halogen; or an amide group (as in (iii) above), in which other substituted phenyl groups may comprise more than one of these substitutents;
- (v) an ester of the form $-O-C(=O)-R^{59}$, wherein $R^{59}$ may comprise a linear or branched alkyl group, for example, $CH_3$;
- (vi) an amine of the form, $-NR^{60}R^{61}$, wherein $R^{60}$ and $R^{61}$ may be independently selected from the following H; $CH_3$; a linear or branched alkyl group; a dialkyl group; or an N-alkylgroup; and
- (vii) 1,2 di-substituted versions of the above, wherein $R^{51}$, $R^{52}$, $R^{53}$, and $R^{54}$ are as defined in (a) and (b) above.

B may comprise a styrene or derivative thereof. However, it is especially preferred that B comprises an acrylate, such that the homopolymer and hence, microgel particles, are preferably, substantially insoluble in water. Hence, B may comprise ethylacrylate (EA). However, most preferably, B comprises methylmethacrylate (MMA). This is described in the Example and illustrated in FIG. 6.

The alkyl group or alkyl chain may comprise a $C_1$-$C_{20}$ chain, and preferably, a $C_1$-$C_{15}$ chain. It is envisaged that the alkyl group or the alkyl chain may comprise a $C_1$-$C_{10}$ chain, and more preferably, a $C_1$-$C_6$ chain, and most preferably a $C_1$-$C_3$ chain. The chain may be straight or branched. However, preferably, the chain is straight. The alkyl group or alkyl chain may be a methyl, ethyl, propyl, butyl, or a pentyl chain.

Hence, in a preferred embodiment, the microgel particle comprises ethylacrylate (i.e. EA, which is the hydrophobic co-monomer, B), methacrylic acid (i.e. MAA, which is the pH responsive co-monomer, P), and 1,4-butanediol diacrylate (i.e. BDDA, which is the functional cross-linking co-monomer, X). Accordingly a preferred particle comprises poly(EA/MAA/BDDA).

The compound poly(EA/MAA/BDDA) of the microgel particle may comprise a maximum mass % EA (hydrophobic monomer) of about 95%, a minimum mass % MAA (pH-responsive monomer) of about 5%, and a minimum mass % BDDA (cross linking monomer) of about 0.1%. However, the preferred compound, (poly(EA/MAA/BDDA) of the microgel particles, comprises about 65.9% EA, about 33.1% MAA and about 1.0% BDDA based on the total monomer mass. This may be defined as a mass ratio of EA/MAA/BDDA as 65.9/33.1/1.0, or as a mole ratio of EA/MAA/BDDA is 130.4/76.0/1.0.

In another preferred embodiment, the microgel particle comprises methylmethacrylate (i.e., MMA, which is the hydrophobic co-monomer, B), methacrylic acid (i.e., MAA, which is the pH-responsive co-monomer, P) and ethyleneglycol dimethacrylate (i.e., EGDMA, which is the functional cross-linking co-monomer, X). Accordingly another preferred particle comprises poly(MMA/MAA/EGDMa).

The compound poly(MMA/MAA/EGDMa) of the microgel particle may comprise a maximum mass % MMA hydrophobic monomer) of about 95%, a minimum mass % MAA (pH-responsive monomer) of about 5%, and a minimum mass % EGDMa (cross linking monomer) of about 0.1%. However, the preferred compound, (poly(EA/MAA/EGDMa) of the microgel particles, comprises about 66.8% MMa, about 32.8% MAA and about 0.4% EGDMa based on the total monomer mass. This may be defined as a mass ratio of MMA/MAA/EGDMa as 167/82/1.0, or as a mole ratio of MMA/MAA/EGDMa is 320/185/1.0.

As mentioned above, the co-monomers may be mixed to form a precursor mix, which may be contacted with an initiator to initiate the polymerisation reaction. If an anionic initiator is used in the preparation of the microgel particles, this will result in the resultant compound containing anionic species, left over from the initiator, which is covalently bonded to the copolymer network.

It is also envisaged that the microgel particle may comprise combinations of B, P and X to produce particles of mixed charge.

The anionic species forms from homolytic scission (i.e., homolysis) of a reactive single bond within the initiator. Homolysis may be caused by heat or irradiation (e.g., UV-light). The fragment reacts with monomer to initiate free-radical polymerisation. In the preferred embodiment the initiator is water-soluble.

The anionic species, may be a fragment such as $-OSO_3^-$ if an inorganic persulfate initiator, such as $[M]S_2O_8^{2-}$ is used, wherein M is a cation such as $K^+$, $Na^+$ or $NH_4^+$, or a divalent cation.

Alternatively, a peroxide initiator may be used to initiate polymerisation. This initiator is defined as $R^{70}-O-O-R^{71}$ wherein $R^{70}$ or $R^{71}$ may be independently selected from a group consisting of H; $CH_3$; a linear or branched alkyl group; a dialkyl group; a N-alkyl group of up to 10 C units; or $C_6H_5$; or $C_6H_4R^{72}$ wherein $R^{72}$ comprises substituents, such as alkyl, $CH_3$, or a halogen, or other substituted phenyl groups comprising more than one of these substituents.

Alternatively, a cationic amine initiator may be used, which may be defined by Formula VI:—

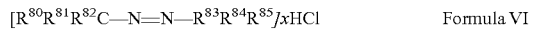

$$[R^{80}R^{81}R^{82}C-N=N-R^{83}R^{84}R^{85}]xHCl \qquad \text{Formula VI}$$

wherein $R^{80}$, $R^{81}$, $R^{83}$ and $R^{84}$ may be independently selected from a group consisting of H; $CH_3$; a linear or branched alkyl group; a dialkyl group; a N-alkylgroup of up to 10 C units; and wherein $R^{82}$ and $R^{85}$ may be $C(-NR^{86})NH_2$ wherein $R^{86}$ may be independently selected from a group consisting of H; $CH_3$; a linear or branched alkyl group.

For example, a specific example is propanimidamide, 2,2'-azobis[2-methyl-, dihydrochloride]. This initiator is also known as V50.

Alternatively, an organic anionic azo initiator may be used, which may be defined by Formula VII:—

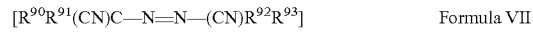

$$[R^{90}R^{91}(CN)C-N=N-(CN)R^{92}R^{93}] \qquad \text{Formula VII}$$

wherein $R^{90}$ and $R^{92}$ may be independently selected from a group consisting of H; $CH_3$; a linear or branched alkyl group; a dialkyl group; a N-alkylgroup of up to 10 C units, and wherein $R^{91}$ and $R^{93}$ may be $CR^{94}COOH$, wherein $R^{94}$ may be $-CH_2-$, $-CH_2CH_2-$ or a linear, or branched, methylene chain up to 20 C chains in length, or $-C_6H_4-$, $C_6H_3R^{95}$ wherein $R^{95}$ comprises a substituent, such as an alkyl group $CH_3$, a halogen; or an amide group; or other di- or tri-substituted phenyl groups containing more than one of these substitutents. For example, a specific example is azobiscyanopentanoic acid (also known as 4,4'-azobis(4-cyanovaleric acid)).

It is preferred that the anionic species comprises an anionic species with low $pK_a$ values, for example, sulphate groups ($-OSO_3^-$) that are covalently bonded to the polymer chains. These groups result from reaction of the initiator with the monomers during polymerisation. However, the anionic species may also originate from incorporation of a co-monomer, which contains sulphate groups, e.g., 2-acrylamido-2-methylpropane sulphate. However, it most preferred that the anionic species is $-OSO_3^-$, which originates from the homolysis fragment of ammonium persulfate.

Preferably, the method for preparing the particles comprises use of a surfactant during preparation of the microgel particle. The surfactant may be substantially non-ionic. For example, such a surfactant may be used when acidic or basic P monomers, and anionic or cationic initiators are used. However, a non-ionic surfactant may be used with other combinations.

The surfactant may be defined by the following formula VIII:—

$$R^{99}R^{100}-O-R^{101}R^{102} \qquad \text{Formula VIII}$$

wherein:
(a) $R^{100}$ may comprise $-CH_2-$, $-CH_2CH_2-$ or a linear, or branched, methylene chain up to 40 C units in length; or $-C_6H_4-$, $C_6H_3R^{103}$ wherein $R^{103}$ comprises a substituents such as an alkyl group; $CH_3$; a halogen; or an amide group; or other di- or tri-substituted phenyl groups containing more than one of these substitutents;
(b) $R^{99}$ and $R^{102}$ may be independently selected from a group consisting of H; $CH_3$; a linear or branched alkyl group; a dialkyl group; a N-alkylgroup of up to 10 C units; or
(c) $R^{101}$ may comprise $-(CH_2CH_2O)_n-$ with n from 1 to 30.

An example illustrating the above is $CH_3(CH_2)_{11}(OCH_2CH_2)_{23}OH$ which is known as Brij 35. The surfactant may be substantially anionic. For example, this may be used when acidic P monomers and anionic initiators are used. However, the surfactant may be used with other combinations.

When the surfactant is an anionic surfactant, it may be defined by the following formula IX:—

$$[R^{110}R^{111}R^{112}Y]^{p-}[cation]^{p+} \qquad \text{Formula IX,}$$

wherein (a) $R^{110}$ may be independently selected from a group consisting of H; $CH_3$; a linear or branched alkyl group; a dialkyl group; a N-alkylgroup of up to 10 C units;

(b) $R^{111}$ may be —$CH_2$—, —$CH_2CH_2$— or a linear, or branched, methylene chain up to 40 C units in length, or may comprise —$C_6H_4$—, $C_6H_3R^{103}$ wherein $R^{103}$ comprises substituents such as an alkyl group; $CH_3$; a halogen; or an amide group or other di- or tri-substituted phenyl groups containing more than one of these substitutents;

(c) optionally, $R^{112}$ may be —$(CH_2CH_2O)_n$— with n from 1 to 30. This unit may also be omitted completely from the surfactant structure; and (d) Y may be an anionic functional group such as: —$OSO_3^-$, —$SO_3^-$, —$COO^-$, —$PO_3^-$.

The total charge of the cation balances that of the anionic chain. It may be $Na^+$, $NH_4^+$ or other mono or divalent anions. A preferred surfactant is sodium dodecylsulfate: $CH_3(CH_2)_{11}OSO_3^-Na^+$ or sodium dodecylbenzene sulfonate: $CH_3(CH_2)_{11}C_6H_4$—$OSO_3^-Na^+$.

The surfactant may be substantially cationic. For example, this would be used when basic P monomers and cationic initiators are used. However, it may be used with other combinations. When the surfactant is a cationic surfactant, it may be defined by the following formula X:—

$$[R^{120}R^{121}NR^{122}R^{123}]^{n+}[Anion]^{n-} \quad \text{Formula X}$$

wherein (a) $R^{120}$, $R^{122}$ and $R^{123}$ may be independently selected from a group consisting of H; $CH_3$; a linear or branched alkyl group; a dialkyl group; a N-alkylgroup of up to 10 C units; and (b) $R^{121}$ may be —$CH_2$—; —$CH_2CH_2$— or a linear, or branched, methylene chain up to 40 C units in length; or —$C_6H_4$—; $C_6H_3R^{124}$ wherein $R^{124}$ comprises a substituent such as an alkyl group; $CH_3$; a halogen or an amide group or other di- or tri-substituted phenyl groups containing more than one of these substituents.

Preferably, the total charge of the anion balances that of the cationic chain. It may be a halide ($Cl^-$, $Br^-$), or other monovalent or divalent anionic species. A preferred example is cetyltrimethylammonium bromide: $CH_3(CH_2)_{15}N(CH_3)_3^+Br^-$.

In addition, the surfactant may comprise a polymeric surfactant. Suitable polymeric surfactants include:—(a) those based on polyethyleneoxide (PEO) and (b) the so-called pluronics which are based on polyethyleneoxide (PEO) and polypropyleneoxide (PPO), i.e., PEO-PPO-PEO. Advantageously, both of these types have been approved by the FDA for use in the body. Another alternative is (c) the polyoxyl castor oil surfactants which are based on polyethyleneoxide (PEO).

It is preferred that the method used for preparing the microgel particles comprises use of a suitable buffer during preparation. The purpose of the buffer is to maintain the pH within regions which aid colloid stability, i.e. pH>3. Suitable buffers that could be used are mixtures of $MH_2PO_4$ and $M_2HPO_4$, wherein M may be independently selected from $Na^+$ or $K^-$ or another monovalent cation. Alternatively, $M_2B_2O_7$ solutions may also be used, where M is defined herein. The preferred buffer is $K_2HPO_4$.

Table 1 below shows an embodiment of the components of a preferred microgel particle based on the polymer: poly(EA/MAA/BDDA)

TABLE 1

Masses and amounts of materials used to prepare poly(EA/MAA/BDDA) microgel (referred to herein as Microgel 1)

| Material | molecular mass/(g/mol) | mass used/g | wt. %[c] | number of moles |
|---|---|---|---|---|
| EA | 100.1 | 143.5 | 65.9 | 1.434 |
| MAA | 86.1 | 72.0 | 33.1 | 0.836 |
| BDDA | 198.2 | 2.2 | 1.0 | 0.011 |
| SDS | — | 1.75 | — | — |
| $K_2HPO_4$ | — | 3.0[a] | — | — |
| APS | 228.0 | 6.25[b] | — | 0.0014 |
| Water | — | 500 | — | — |
| Total | | 728.7 | | |

[a]Added as a 7% solution in water.
[b]Added in two portions (dissolved in water)
[c]by monomer.

It will be appreciated that the ratios of the different monomer in poly(EA/MAA/BDDA) may vary. It is preferred that the maximum mass % EA (hydrophobic monomer) is about 95%; the minimum mass % MAA (pH-responsive monomer) is about 5%; and the minimum mass % BDDA (cross linking monomer) is about 0.1%.

It is preferred that poly(EA/MAA/BDDA) contains about: 65.9% EA, 33.1% MAA and 1.0% BDDA based on the total monomer mass. (or as a mass ratio of EA/MAA/BDDA is 65.2/32.7/1.0; or as a mole ratio of EA/MAA/BDDA is 130.4/76.0/1.0)

Tables 2 and 3 show two variants (referred to herein as Microgels 2A and 2B respectively) of the components of another preferred microgel particle based on the polymer: poly(MMAA/MAA/EGDMa)

TABLE 2

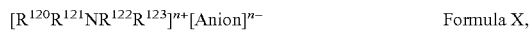

Masses and amounts of materials used to prepare poly(MMA/MAA/EGDMa) microgel (Microgel 2A)

| Material | molecular mass/(g/mol) | mass used/g | wt. %[a] | number of moles |
|---|---|---|---|---|
| EA | 100.1 | 185.4 | 64.0 | 1.85 |
| MAA | 86.1 | 103.4 | 35.7 | 1.2 |
| EGDMa | 198.2 | 0.78 | 0.3 | 0.0039 |
| SDS | — | 1.75 | — | — |
| $K_2HPO_4$ | — | 0.179 | — | — |
| APS | 228.0 | 0.232 | — | — |
| Water | — | 500 | — | — |
| Total | | 791.7 | | |

[a]by monomer

TABLE 3

Masses and amounts of materials used to prepare poly(MMA/MAA/EGDMa) microgel (Microgel 2B)

| Material | molecular mass/(g/mol) | mass used/g | wt. %[a] | number of moles |
|---|---|---|---|---|
| EA | 100.1 | 125.6 | 67.4 | 1.25 |
| MAA | 86.1 | 58.7 | 31.5 | 0.68 |
| EGDMa | 198.2 | 1.94 | 1.0 | 0.0098 |
| SDS | — | 0.32 | — | — |
| NaCl | 58.4 | 0.44 | — | — |
| $K_2HPO_4$ | — | 0.179 | — | — |
| APS | 228.0 | 0.232 | — | — |
| Water | — | 500 | — | — |
| Total | | 687.4 | | |

[a]by monomer

Hence, the composition used in the first aspect or in the second aspect comprises microgel particles as defined above, in which the co-monomers comprise mixtures of three monomers selected from: EA, MAA, MMA, EGDMa and BDDA. It is preferred that the co-monomers are mixed together to form a co-monomer pre-mix. The preferred initiator such as Ammonium persulphate is then added, in the presence of the surfactant SDS, and the buffer di-potassium hydrogenphosphate. The Example provides specific details of a preferred embodiment for preparing the pH responsive microgel particles.

The inventors envisage that the medicament of the first aspect, or the method of the second aspect may be used to repair any damaged, or degenerated soft tissue in a subject. Examples of suitable soft tissues which may be treated include skin, muscle, ligament, or fat. Such damaged or degenerated soft tissue may comprise a wound, which may be either acute or chronic. However, it is preferred that the soft tissue being treated comprises damaged or degenerated load-bearing tissue. The skilled technician will appreciate that key load-bearing sites in the body, which may require treatment include any articular joint, for example, the hip, elbow, ankle, knee, wrist, etc.

However, it is most preferred that the medicament according to the first aspect or the method of the second aspect are used to treat damaged or degenerated vertebral, or intervertebral discs (IVDs). Preferably, the method of the second aspect comprises administering the composition directly into the IVD, and preferably into the nucleus pulposus (NP) thereof. Hence, advantageously, no surgery is required using the method. More preferably, the composition may be administered directly into clefts, which form when the proteoglycan content in the IVD decreases with age. Furthermore, it is preferred that the composition or medicament may be administered by injection into the target tissue.

It is especially preferred that the pH of load-bearing tissue being treated is at a pH sufficiently different to the pH of the composition before administration, wherein upon administration of the composition, the change in pH induces the change in conformation of the microgel particles, and preferably, causes swelling thereof to form the gel. For example, if the composition or medicament is being administered to an IVD in a subject, it is known that the average pH of the IVD is about 6.6. Hence, it is preferred that the particles are maintained at a pH of less than 6.6, such that upon administration into the IVD, the particles will swell and cause gelation of the composition. Preferably, the particles are maintained at a pH of between about 5.0-6.6, more preferably, between about 5.5-6.6, and even more preferably, between about 6.0-6.6 before administration. Accordingly, the increase in pH from less than 6.6 to about 6.6 in vivo causes water to enter the particles such that they swell, thereby causing a gel to form.

However, in one embodiment of the method, it may be preferred to contact the composition comprising the microgel particle with either an acid or base such that the variation in pH is accelerated thereby accelerating gelation in vivo. It will be appreciated that an acid is added if it is desired to decrease the pH of the particles for gelation to occur, and an alkali is added if it is desired to increase the pH for gelation to occur. It will be appreciated that the acid or alkali may be administered to the target tissue either before or after the composition comprising the microgel particle has been administered. Hence, the method may further comprise administering to the subject a suitable amount of an alkali, wherein gelation is accelerated upon contact with the composition. The alkali may either be added to the tissue before the composition, so that gelation occurs, or after the composition is added so that gelation occurs. Alternatively, a co-administration procedure may be used where both the composition comprising the microgel particle dispersion, and alkali are administered substantially at the same time. This may be achieved for example through a specially constructed syringe needle.

However, where the composition is being administered to an IVD, it is important to note that administration of alkali is not essential because the buffering action of the IVD will gradually increase the pH to 6.6 such that gelation occurs automatically. It will be appreciated that such automatic gelation is greatly advantageous as there is no need to exogenously add any alkali to the subject.

Hence, as a result of administration of the composition to the subject, there is preferably, an increase in disc height and also the Young's Modulus of the IVD, and the mechanical strength is effectively restored. Advantageously, this is a minimally invasive method that can fill the interior of irregularly shaped clefts in the IVD. Hence, this minimally invasive method does not involve any major surgical intervention, thereby meaning the subject being treated has a much curtailed recovery time. In addition, because the particles used in the composition according to the invention are preformed (i.e. the polymers are cross-linked) prior to use, there is no requirement to administer any initiators, or further monomers for any in vivo polymerisation to occur. Another advantage of the method is that it does not require removal of any healthy tissue. This is in direct contrast to nucleus replacement technologies involve microdisectomy and removal of nucleus pulposus tissue.

In another embodiment, the composition used in the first aspect or in the method of the second aspect may comprise at least one nucleus pulposus cell and/or at least one stem cell and/or at least one mammalian cell.

Examples of suitable mammalian cells, which may be added to the composition include chondrocytes (e.g. autologous or autogenous). Examples of suitable stem cells, which may be added to the composition include mesenchymal, haematopoeic etc., including embryonic and cloned stem cells. In addition, the composition may further comprise collagen and/or proteoglycans.

It will be appreciated that adding nucleos pulposus cells to the composition will increase the rate of recovery of the subject. Hence, a further advantage of the method according to the invention is that it allows mixing of living cells (e.g, NP cells or stem cells) with the composition comprising the microgel particle dispersion in order to facilitate re-growth of NP tissue. Thus, the method according to the invention is amenable to combining mechanical support with a biological repair system.

Preferred disease conditions, which may be treated with the medicament of the first aspect or the method according to the second aspect include arthritis, intervertebral disc degeneration, back pain, low back pain, sciatica, cervical spondylosis, neck pain, kyphosis, scoliosis, degenerative joint disease, osteoarthritis, spondylolysis, spondylolisthesis, prolapsed intervertebral disc, failed spine surgery, and spinal instability. The disease condition may be chronic or acute, for example, chronic or acute back pain.

In a most preferred embodiment, the composition used in the first aspect of the invention is preferably colloidally stable (i.e. the microgel particles are dispersed on the colloidal scale) prior to the exposure to the variation in pH. Preferably, the particles are substantially collapsed prior to exposure to the variation in pH. Therefore, preferably, the composition is substantially fluid at a pH, which is less than physiological pH (i.e., prior to administration), and therefore may be injected into the subject. However, it is not an essential requirement that the composition remains colloidally stable once it is administered to the subject, for example, injected into the NP. It is preferred that the particles are negatively charged at physiological pH, i.e. about 7.4. Hence, preferably, the particles are operable to swell when exposed to physiological pH. Hence, following administration, the composition preferably forms a gel, which does not flow at physiological pH. Preferably, the composition is used to treat damaged or degenerated IVD.

Therefore, in a preferred embodiment of the invention, the composition and hence, particles are maintained at a pH of about 4.0-6.0, and preferably, about 5.5, prior to administration. Hence, preferably, the diameter of the particles prior to exposure to the pH variation is between about 50-100 nm, and most preferably, about 65 nm (as measured by Scanning Electron Microscopy). Hence, the composition is substantially fluid, such that it may be administered to the tissue needing repair, for example, by injection into the clefts of the NP of the IVD. The pH in the IVD is about 6.6, and so the increase in pH from about 5.5 before administration to about 6.6 after administration causes the diameter of the particles to increase to about 300-350 nm, and most preferably, about 320 nm. At this diameter, the composition forms a gel in the tissue and thereby provides load-bearing properties to the IVD.

The swelling pressure of the particles can be adjusted using pH in order to increase the effective Young's Modulus of the microgel-loaded soft tissue. Furthermore, the inventors believe it should be possible to adjust the $pK_a$ of these microgels by varying the chemical composition of the particles, which will allow fine-tuning of the load-bearing properties of these materials at the pH of the damaged load-bearing tissue.

It will be appreciated that the composition according to the present invention may be used in a monotherapy (i.e. use of the microgel particle according to the invention alone to prevent and/or treat diseases characterised by damaged or degenerated soft tissue, and preferably, load-bearing tissue). Alternatively, the microgel particle according to the invention may be used as an adjunct, or in combination with known therapies.

The composition comprising the microgel particle may have a number of different forms depending, in particular, on the manner in which the composition is to be used. Thus, for example, the composition may be in the form of a liquid, ointment, cream, aerosol, spray, micelle, transdermal patch, or any other suitable form that may be administered to a subject being treated in a hydrated or moist form. The subject may be an animal or person. It will be appreciated that the vehicle of the composition should be one which is well tolerated by the subject to whom it is given, and preferably enables delivery of the composition and hence, at least one microgel particle, to the target soft tissue.

Compositions comprising the microgel particle according to the invention may be used in a number of ways. Preferably, the composition may be administered by injection.

The composition comprising the microgel particle may be incorporated within a slow or delayed release device. Alternatively, a therapeutic agent such as a drug molecule may be incorporated within the microgel particle, and the agent may be slowly released. Such devices may, for example, be inserted on or in the target load-bearing tissue, and the composition or therapeutic agent may be released over minutes, days, weeks, or even months. Such devices may be particularly advantageous when long-term treatment with the composition comprising a microgel particle (or therapeutic agent in the particle) according to the invention is required, and which would normally require frequent administration (e.g. at least daily injection).

It will be appreciated that the amount of composition, and hence, amount or number of microgel particles that is required is influenced by the degree of damage of the load bearing tissue being treated. In addition it will be influenced by its biological activity and bioavailability, which in turn depends on the mode of administration, the physicochemical properties of the microgel particle employed and whether the microgel particle is being used as a monotherapy, or in a combined therapy. The frequency of administration will also be influenced by the above-mentioned factors and particularly the half-life of the microgel particle, within the subject being treated.

Optimal dosages to be administered may be determined by those skilled in the art, and will vary with the microgel particle in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the microgel particle according to the invention and precise therapeutic regimes (such as daily, weekly or monthly doses of the composition and hence, microgel particle, and the frequency of administration).

It will be appreciated that the dose of composition and hence, microgel particle is highly dependent on the target tissue, and the disease being treated. However, generally, a daily dose of between 0.01 µg/kg of body weight and 0.5 g/kg of body weight of the composition according to the invention may be used for the prevention and/or treatment of a disease characterised by damaged load bearing tissue, depending upon which specific microgel particle is used. More preferably, the daily dose is between 0.01 mg/kg of body weight and 200 mg/kg of body weight, and most preferably, between approximately 1 mg/kg and 100 mg/kg.

The actual concentrations of medicament or composition to be used can be expressed as a wt. % of microgel with respect to the total mass of the dispersion. Hence, it is preferred that the concentration of microgel with respect to the total mass of the dispersion is between 1 and 70 wt %. It is more preferred to be between 10 and 40 wt. %, and more preferably, to be upon administration between 15 and 25 wt. %. The preferred embodiment comprises use 20 wt. % microgel with respect to the total mass of the dispersion.

It should be appreciated that the preferred use of the composition is for treating damaged or degenerated IVD, and preferably the NP thereof. Hence, the mass of composition injected into the degenerated NP (this includes water and polymer particles) will be such that the final wt. % of microgel dispersion will comprise between 0.5 and 70% wt. of the total mass of the NP containing microgel dispersion. It is more preferred that the microgel dispersion comprises between 10 and 30% by mass of the NP containing injected microgel.

Daily doses may be given as a single administration (e.g. a single daily injection). Alternatively, the composition used may require administration twice or more times during a day. As an example, the composition according to the invention may be administered as two (or more depending upon the severity of the condition) daily doses of between 5 mg and 7000 mg (i.e. assuming a body weight of 70 kg). A patient receiving treatment may take a first dose upon waking and then a second dose in the evening (if on a two dose regime) or at 3 or 4 hourly intervals thereafter. However, it is most preferred that a slow release device may be used to provide optimal doses of the composition to a patient without the need to administer repeated doses. Preferably, injections are into the spine. They will require a skilled clinician to be done properly and it is preferred that only one injection is required. However, it may be that more than one injection is required.

This invention provides a pharmaceutical composition comprising a therapeutically effective amount of a microgel particle according to the invention and optionally, a pharmaceutically acceptable vehicle. In one embodiment, the mass of the microgel particles (calculated on a dry weight basis) is an amount from about 0.01 mg to about 800 mg. In another embodiment, the amount of the particle is an amount from about 0.01 mg to about 500 mg. In another embodiment, the amount of the particle is an amount from about 0.01 mg to about 250 mg. In another embodiment, the amount of the particle is an amount from about 0.1 mg to about 60 mg. In another embodiment, the amount of the particle is an amount from about 0.1 mg to about 20 mg.

The invention further provides a process for making a pharmaceutical composition comprising combining a therapeutically effective amount of a microgel particle according to the invention, and a pharmaceutically acceptable vehicle. A "therapeutically effective amount" is any amount of a microgel particle according to the invention which, when administered to a subject provides prevention and/or treatment of a disease characterised by damaged or degenerated soft tissue. However, it will be appreciated that the type and amount of the microgel particle will contribute to the therapeutic efficacy of the particle. A "subject" may be any vertebrate, mammal, domestic animal or human being.

A "pharmaceutically acceptable vehicle" as referred to herein is any physiological vehicle known to those of ordinary skill in the art useful in formulating pharmaceutical compositions. In a preferred embodiment, the pharmaceutical vehicle is a liquid, and the pharmaceutical composition is in the form of a dispersion.

Liquid vehicles are used in preparing solutions, suspensions, emulsions, syrups, elixirs and pressurized compositions. Hence, the microgel particle may be dispersed or suspended in a pharmaceutically acceptable liquid vehicle such as water, an organic solvent, a mixture of both, or pharmaceutically acceptable oils or fats. The liquid vehicle may comprise other suitable pharmaceutical additives, such as solubilisers, emulsifiers, buffers, preservatives, suspending agents, thickening agents, colours, viscosity regulators, stabilisers or osmo-regulators.

Suitable examples of liquid vehicles for parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle may also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

Liquid pharmaceutical compositions, which are sterile solutions or suspensions may be utilized by for example, intramuscular, intrathecal, epidural, intraperitoneal, subcutaneous, and particularly, intravenous injection. Hence, the composition comprising the microgel particle may be prepared as a sterile solid composition that may be dispersed or suspended at the time of administration using sterile water, saline, or other appropriate sterile injectable medium. Vehicles are intended to include necessary and inert binders, suspending agents, lubricants, preservatives, dyes, and coatings.

The composition according to the invention may be administered in the form of a sterile dispersion or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

In a further aspect there is provided a pH-responsive microgel particle comprising a plurality of cross-linked polymers, wherein at least one polymer comprises a chemical species, which species is responsive to pH so as to cause the particle to swell in response to a pH change.

Preferably, the particle is less than 10 µm in diameter, and preferably, less than 1 µm. The inventors believe that, to date, no-one has used such pH responsive particles in the medical application envisaged above (i.e., for soft-tissue repair). Accordingly, in a further aspect there is provided a pH-responsive microgel particle comprising a plurality of cross-linked polymers, wherein at least one polymer comprises a chemical species, which species is adapted to respond to a variation in pH to thereby cause the particle to swell, for use as a medicament.

Such particles as described herein will have specific medical applications for treating any disease characterised by damaged or degenerated load bearing tissue. Hence, in a still further aspect there is provided a pH-responsive microgel particle comprising a plurality of cross-linked polymers, wherein at least one polymer comprises a chemical species, which species is adapted to respond to a variation in pH to thereby cause the particle to swell, for the manufacture of a medicament for treating a disease characterised by damaged or degenerated soft tissue.

Preferably, the soft tissue comprises load bearing tissue, for example the IVD.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows the variation of the hydrodynamic diameter of the microgel particles 1, 2A and 2B as a function of pH. The data were recorded using particles dispersed in 0.001 M $NaNO_3$;

FIG. 2 is a photograph of bovine IVD unit after dissection. The gelled microgel is indicated by the arrow. In this case, 1 M NaOH was injected immediately after microgel injection to give a final pH of 6.5;

FIG. 3 shows the variation of relative disc height with stress during loading and unloading. The bovine IVD unit contained microgel adjusted to pH=6.5. The arrows indicate loading and unloading cycles. The relative height is the height of the IVD unit measured under a given compressive stress to that of the unit before load was applied;

FIG. 4 shows the variation of (a) relative height measured and (b) nominal modulus measured at 0.5 MPa, as a function of cycle number for bovine units injected with PBS and microgel. Controls are normal disc (Normal), and disc injected with PBS (PBS). The legend shows the pH values. Error bars are shown for one data set for clarity;

FIG. 5 shows the variation of relative height ($H_r$) measured at 0.5 MPa as a function of cycle number for bovine units injected with PBS and microgel. Controls are normal disc (Normal), disc injected with PBS (PBS) and without any injection (Collagenase);

FIG. 6 shows details of a monomers used for preparing the microgel particles according to the invention; and FIG. 7. Optical micrographs of annulus fibrosus (AF) cells in contact with (a) agar, (b) Microgel 1, (c) Microgel 2A and (d) Microgel 2B. The micrographs were taken after 24 h of contact.

EXAMPLES

The inventors prepared a series of pH-responsive polymer gel microparticles, which were first characterised as shown in FIG. 1, and then investigated to see if they could be used for repairing damaged intervertebral disks, as shown in FIG. 2. The microparticles were injected into the nucleus pulposus of vertebral units obtained from the tails of freshly slaughtered bovine animals, the heights of which were then measured to determine the compression values thereof following treatment as shown in FIGS. 3-5. FIG. 6 shows the preferred materials used to prepare the microgel.

Materials and Methods
(i) Preparation of pH-Responsive Microgels
(a) Microgel 1 (—See Table 1)

Poly(EA/MAA BDDA) microgel was prepared using seed-feed emulsion polymerisation (Macromolecules, 1994, 27, 6642). A monomer mixture containing Ethylacrylate (EA) (Aldrich, 143.5 g), Methacrylic acid (MAA) (Aldrich, 72.0 g) and 1,4-butanediol diacrylate (BDDA) (Aldrich, 2.2 g) was prepared and 12.5% of the mixture added to a pre-purged, stirred, solution of sodium dodecylsulphate (BDH, 1.75 g in 500 g of water), which had been heated to 80° C. The monomers were passed over an alumina column prior to use. $K_2HPO_4$ (3 g of 7% solution in water) and ammonium persulphate (2.95 g of 5% solution in water) were immediately added whilst maintaining a nitrogen atmosphere. After appearance of a slight blue turbidity, the remaining monomer mixture was added at a continuous rate over a 90 min period. Additional initiator (3.3 g of 5% solution in water) was added and the temperature maintained for a further 2 h. The microgel was extensively dialysed against Milli-Q quality water. The average particle size of the particles in the collapsed state was about 65 nm. The swollen state diameter was about 220 nm at pH=7.4.

(b) Microgel 2A (—See Table 2)

Poly(MMA/MAA/EGDMa) microgel (Microgel 2A) was prepared using seed-feed emulsion polymerisation. A seed monomer mixture containing Methyl methacrylate (MMA) (Aldrich, 139.3 g), Methacrylic acid (MAA) (Aldrich, 60.1 g) and Ethyleneglycol dimethacrylate (EGDMa) (Aldrich, 2.1 g) was prepared and 25.2 g (8.8% of total monomer) of the mixture added to a pre-purged ($N_2$), stirred, solution of sodium dodecylsulphate (BDH, 1.75 g in 500 g of water), which had been heated to 80° C. $K_2HPO_4$ (2.55 g of 7% w/w solution in water) and ammonium persulphate (4.50 g of 3% w/w solution in water) were immediately added whilst maintaining a nitrogen atmosphere. A feed monomer mixture containing MMA (273.1 g), MAA (134.0 g) and EGDMa (1.7 g) was prepared. After the appearance of a slight blue turbidity, 264 g (91.2% of total monomer) of the feed monomer mixture was added at a constant rate over a 90 min period. Additional ammonium persulphate (2.73 g of 3% solution in water) was added and the temperature maintained for a further 2 h. The microgel was extensively dialysed against Milli-Q quality water. The average particle size of the particles in the collapsed state was about 100 nm. The swollen state diameter was about 260 nm at pH=7.4

(c) Microgel 2B (—See Table 3)

A variation of the method used to prepare Microgel 2A (above) was also used. Poly(MMA/MAA/EGDMa) microgel was prepared using seed-feed emulsion polymerisation. A seed monomer mixture containing Methyl methacrylate (MMA) (Aldrich, 125.6 g), Methacrylic acid (MAA) (Aldrich, 58.7 g) and Ethyleneglycol dimethacrylate (EGDMa) (Aldrich, 1.94 g) was prepared and 14.0 g (7.5%) of the mixture added to a pre-purged ($N_2$), stirred, solution of sodium dodecylsulphate and sodium chloride (BDH, 0.14 g and Aldrich, 0.44 g respectively, in 200 g of water), which had been heated to 80° C. $K_2HPO_4$ (2.56 g of 7% w/w solution in water) and ammonium persulphate (2.57 g of 5% w/w solution in water) were immediately added whilst maintaining a nitrogen atmosphere. The remaining monomer mixture 172 g (92.5%) was added to a stirred solution of sodium dodecylsulphate (BDH, 0.17 g in 300 g of water). After one hour of reaction, the feed monomer mixture, under constant stirring, was added to the reaction at a constant rate over a 105 min period. The reaction temperature was maintained for a further 2 h. The microgel was extensively centrifuged and washed with Milli-Q quality water. The average particle size of the particles in the collapsed state was about 250 nm. The swollen state diameter was about 700 nm at pH=7.5 (1425 nm at pH=8.1).

(ii) Microgel Characterisation

Photon correlation spectroscopy measurements were performed using dispersions containing 0.03 wt. % of microgel. The measurements were conducted using a BI-9000 Brookhaven light scattering apparatus (Brookhaven Instrument Cooperation), fitted with a 20 mW HeNe and the detector was set at 90° scattering angle.

(iii) Tissue Preparation and Procedure for Microgel Injection

All experiments were conducted using vertebral units obtained from the tails of freshly slaughtered bovine animals, which were less than 2 years old. The tails were obtained from an abattoir, dissected on the day of slaughter and stored in a freezer at 193 K before use. It has been established in other work that freezing of IVDs does not adversely affect the mechanical properties. The units were allowed to thaw and hydrate in phosphate buffered saline (0.15 M) at room temperature for 6 h prior to investigation. Units for investigation were carefully sawed through the cartilaginous endplates so that the nucleus pulposus (and surrounding tissue) was between two parallel endplates. During this process extraneous muscle and ligaments were removed. The NP cross-sectional area was calculated from dissection and the NP height was determined from x-ray photographs of the units. The height of the vertebral pieces was measured from centres of the convex end plates when viewed from the sides. The units were washed and stored in PBS. With the exception of an untreated sample, all NP's were treated by collagenase injection (at a concentration of 10 mg/ml) and degeneration allowed to proceed for 18 h at 37° C. The units were degenerated by injection of 0.2 ml of Type I Collagenase injection (1% w/w). The units were stored at 37° C. in PBS for 18 h during the degeneration stage.

(iv) Injection Procedure

The microgel dispersions (20% w/w) were injected (ca. 0.4 ml) into the degenerated NPs. This was followed by injection of concentrated sodium hydroxide solution (ca. 0.1 ml) into the same region of the NP. This was done to accelerate the process pH equilibration. Microgel dispersions were also injected without added base for comparison. The total injected microgel volume was ca. 0.5 ml in this case. It should be noted that for applications in vivo, the injection of sodium hydroxide would not be required as the natural buffering action of body fluid will increase the pH over time. The injection holes were sealed using Super Glue prior to load measurements. The load measurements were performed within 2 h of microgel injection.

(v) Compression Measurements

The bovine units containing injected microgel were placed under compression using a servo-hydraulic testing instrument (Zwick Roell-Amster), which was fitted with a 1 kN load cell. This unit had a purpose-built load cell that consisted of a cylindrical plunger with a flat stainless steel surface with a raised rim to locate the upper endplate. The lower endplate was located on the floor of a Perspex bath. The maximum load applied to the discs was 1 kN. This gave stresses that covered the range of those experienced by human IVDs under normal conditions. The compression measurements were performed whilst the units were fully immersed in PBS. The first load cycle employed (Cycle 1) was a conditioning cycle, which removed excess water from the IVDs. All units were treated in the same way. Compressive stresses were applied during Cycle 1 until a strain of ca. 0.2 was achieved. Higher stresses were used in subsequent cycles (e.g., see FIG. 3). Considerable care was used to ensure that the structure remained parallel prior to and during the compression measurements. The experimental arrangement corresponded to uniaxial compression. Because there was no constraint on radial expansion during compression the gradients of the stress vs. strain plots gave values for the Young's modulus (J. Appl. Polym. Sci. 1968, 12, 1147). The strain values were calculated from the displacement divided by height measured immediately prior to commencing a compression cycle.

(vi) Cell Viability Studies

All gelled microgel dispersions were prepared at least 24 h prior to cell viability studies. Agar (1.5 w %) was dissolved in deionised water by microwave heating and then allowing to cool to from a homogenous gel. This was used as a control. The gelled microgel dispersions were prepared by adding sufficient 2M NaOH to form a stiff, swollen gel having $\phi_p=0.10$. Adherent cultured human articular fibrosus (AF) cells were used to test cell viability. They were washed free of media with phosphate buffered saline (PBS). The cells were incubated for about 2 minutes with 5 ml trypsin which was then deactivated with 5 ml complete media (DMEM). The resultant suspension containing free floating AF cells was centrifuged and the supernatant was removed and the cell pellet resuspended in about 5 ml fresh media. The cells were allowed to grow on the bottom of tissue culture wells for 24 h and then samples of gelled microgel placed on top of them in the presence of medium. This ensured contact of the gels with the cells. After predetermined exposure times the cells were viewed from beneath the well plate using optical microscopy.

Results

Referring to FIG. 1, there is shown the variation of the hydrodynamic diameter (d, measured in nanometers) of the microgel particles (1, 2A and 2B) as a function of pH. The data were recorded using particles dispersed in 0.001 M $NaNO_3$. FIG. 1 shows that the particles exhibited a substantial increase in particle size (diameter) with pH from about 75 nm at pH 4.0 to about 300 nm at pH 10. The $pK_a$ for the microgels is estimated at about 7.0. This is attributed to the EA or MMA monomers. The $pK_a$ for pH-responsive polymers is believed to increase with hydrophobic co-monomer content due to aggregation of the hydrophobic groups, which opposes swelling. The phase transitions of microgel dispersions containing a polymer volume fraction ($\phi_p$) of 0.10 were also investigated as a function of pH. The dispersions were colloidally stable at pH=4. A fluid-to-gel transition occurred above pH=6.0 due to particle swelling. Oscillatory rheological studies (not shown) revealed that strong physical gels formed with elastic modulii greater than $10^3$ Pa and tan δ values less than 0.15.

Vertebral bovine tail units were used as model IVDs because they have similar structures to human IVDs, and can be subjected to meaningful biomechanical stresses and can be obtained without degeneration. Reproducible extents of degeneration were introduced by injecting collagenase (a collagen cleaving enzyme) into the Nucleus Pulposus. The microgel dispersion (pH=4.0) was subsequently injected into the degenerated NPs (using $\phi_p$ values of 0.20). It was not feasible to allow the microgels to equilibrate to the pH of the model IVDs (ca. 7.4) because of the certainty of significant natural tissue decomposition over an extended time period. Hence, concentrated NaOH solution (1 M or 2 M) was injected into the same region of the NP immediately after microgel injection to accelerate neutralisation. This gave nominal $\phi_p$ values of 0.16. It should be appreciated that injection of a base (alkali) would not be necessary in the body where a gradual equilibration of the pH to that of the IVD would occur. The pH of the IVD is about 6.6 (Spine 1992, 17, 1079).

Measurements after the compression studies showed that the NPs containing microgel and injected 1 M or 2 M NaOH had, respectively, pH values of 6.5 and 7.0. The total injected volume of microgel and base as a fraction of the NP volume was about 0.25.

Referring to FIG. 2, there is shown a photograph of a bovine unit after dissection, and injection with the microgel. The gelled microgel is indicated by the arrow. In this case, 1 M NaOH was injected immediately after microgel 1 injection to give a final pH of 6.5. Hence, FIG. 2 shows that a gelled microgel phase is clearly evident in this treated NP.

The bovine units were uniaxially compressed at a rate of about 1 mm/min in a cyclic manner. Referring to FIG. 3, there is shown the variation of relative height ($H_r$) with stress during loading and unloading. The bovine unit contained microgel adjusted to pH=6.5. The arrows indicate loading and unloading cycles. Hence, FIG. 3 shows the relative height ($H_r$) versus stress data from selected cycles for a unit containing microgel 1 with a pH of 6.5. The relative height has been defined above. The compressive stress is the applied load per unit cross-sectional area. This is based on the cross-section of the disc, which was measured by dissection after the measurements. The $H_r$ value is the ratio of the vertebral unit height measured under a given load to that measured prior to loading. The compressive stress was calculated from the load and the initial cross-sectional area of the NP. It can be seen from FIG. 3 that hysteresis and creep are present. These effects have been observed in related work using untreated bovine IVDs.

Hysteresis is the lack of superposition of the loading and unloading cycles. The hysteresis is due to the rate of linear swelling due to water uptake during unloading being slower than the rate at which the load was removed ca. 1 mm/min. The creep is a consequence of tissue deformation that occurs which is irreversible over the timescale of these measurements. This is a well-known occurrence for IVDs. The creep is time-dependent. In living IVDs, the creep is normally fully recovered after load removal if sufficient time is allowed. This is why the height of humans increases as a result of sleeping.

Referring to FIG. 4, there is shown the variation of (a) relative height measured (variation of $H_r$) and (b) nominal modulus measured at 0.5 MPa as a function of cycle number for bovine units injected with PBS and microgel 1 at different pH values. These values were obtained from displacement vs. load data and IVD dimensions. The $H_r$ and modulus values were measured at a loading (compressive) stress that corresponds to that IVDs experience during light exercise (i.e. about 0.5 MPa). Control data are also presented for a Normal (untreated) unit (i.e. shown as circles in the Figure) and a NP containing injected PBS solution ($\phi_p$=0.16), (i.e. shown as triangles in the Figure).

It can be seen from FIG. 4a that microgel injection restores the relative disc height of the model IVDs to normal values. The microgel, which was treated with alkali/base (pH=6.5 and 7.0), exhibited a cessation of creep after the first few cycles. This differed markedly from the PBS control in which the relative disk height was substantially lower. The increase of the pH (from 4.0) after microgel (and base) injection causes the microgel particles to swell and fill the clefts within the degenerated NPs. The microgel's swelling pressure opposes further compression, thereby providing a resistant force.

It will be appreciated that the Young's Modulus is the ratio of the stretching force, as on the test specimen, per unit cross-sectional area to the elongation per unit length. The Young's Modulus values shown in FIG. 4b were calculated from the instantaneous gradients of the respective stress vs. strain curves (not shown). For homogeneous materials, each value would correspond to a Young's modulus in axial compression. However, they are considered as a nominal modulus for these heterogeneous units. It can be seen that the modulus generally increases as the number of load cycles increases. The modulus for NPs is believed to have contributions from that of the solid tissue matrix and a hydrostatic pressure due to trapped water that is gradually expelled under load. The increase in modulus with cycle number is attributed to loss of water and greater contribution from the compacted tissue and microgel. It can be seen from FIG. 4b that the microgel increases the modulus of damaged NPs to values comparable to and surprisingly even better than those for normal tissue.

The results for the pH=7.0 system are remarkable as a constant modulus, with superior load-bearing capability is achieved after only one load cycle. The data shown in FIGS. 4a and 4b also show that the mechanical properties can be adjusted by pH. Alternatively, if pH was fixed (which is the case in the body) it is likely that $pK_a$ adjustment via microgel composition could be used to adjust the modulus. The $pK_a$ should approach ca. 5.5 with decreasing EA content.

It can be seen from FIG. 4a that the improvement in $H_r$ due to microgel injection was about 0.14 after five load cycles. If these results were to be found in human IVDs, where an average disc height in a person over 50 years old is ca. 6-7 mm), then microgel injection could increase disc heights by about 1 mm during light exercise (compressive stress of about 0.5 MPa). An increase in disc height of this magnitude could make a significant difference to persons suffering from back pain due to degenerated discs.

FIG. 5 is similar to FIG. 4a, showing the relationship of the height of a disc (height relative to the unloaded height) measured at 0.5 MPa as a function of compression cycle. The controls shown in this Figure are normal disc (Normal), disc injected with PBS (PBS), and without any injection (Collagenase). The microgel was injected without added base (Microgel), and with added base to adjust the pH to 6.5 and 7.0. The data show a clear improvement of disc height upon addition of microgel under load. Increase of the pH to 6.5 and 7.0 gives the greatest improvement in disc height.

FIG. 7 shows optical micrographs of the AF cells viewed from beneath the well plates after 24 h of contact with the gelled microgel or agar (control). The images (FIG. 7(b)-(d)) show cells with similar morphology to those exposed to agar (FIG. 7(a)). This indicates that the cells were viable after 24 h of contact. By contrast exposure of the cells to surfactant caused the cells to die within one hour of contact and the morphology observed was rounded. In other experiments not shown here it was found that the AF cells remained viable for at least 5 days when in contact with the gelled microgel dispersions of microgels 1, 2A and 2B. These results indicate that the gelled microgel dispersions are biocompatible with human IVD tissue.

CONCLUSIONS

The inventors have demonstrated for the first time that pH responsive microgels can be used to restore the disc height and modulus of degenerated NPs simply by using an injection. This is a completely new method for using microgels as biomaterials. The swelling pressure of the microparticles can be adjusted using pH in order to increase the modulus of the microgel-loaded NP. The inventors believe it should be possible to adjust the $pK_a$ of these microgels using compositional variation, which will allow fine-tuning of the load-bearing properties of these materials at the pH of the NP, or any other tissue.

It will be appreciated that a key advantage of the invention is that because the pH of the IVD is about 6.6, then providing the microgel particles are maintained at a pH below pH6.6, then upon administration, they will automatically swell and form a gel. Hence, there is no need to add an alkali to the tissue being treated.

It follows from this study that injectable, responsive microgels could be used to support biomechanical loads in other soft tissue types (e.g., cartilage), or in articular joints (e.g., the knee and hip). The inventors also believe that compositional and formulation variation can be used to alter the load-bearing properties of the microgels.

Furthermore the work presented in FIG. 7 illustrate that human cells are viable in the presence of microgels according to the invention and that the composition will therefore be biocompatible for use in human subjects.

The invention claimed is:

1. A method of introducing a composition into a subject in need thereof comprising:
   (i) providing a composition comprising a dispersion comprising pH-responsive microgel particles, wherein the microgel particles have a diameter between 1 nm to 10 μm prior to introduction into the subject and the microgel particles comprise a polymer of pH-responsive co-monomer units and functional cross-linked co-monomer units; and
   (ii) injecting an effective amount of the composition into a tissue selected from the group consisting of a vertebral disc, an invertebral disc, a nucleus pulposus, clefts of a nucleus pulposus of an intervertebral disc, an articular joint, a hip joint, an elbow joint, an ankle joint, a knee joint, a wrist joint, and cartilage, so as to introduce the composition into the subject.

2. The method according to claim 1, wherein the pH of the composition prior to injection is less than the pH of the tissue into which the composition is injected.

3. The method according to claim 1, wherein the pH of the composition prior to injection is between about 4.5-6.0.

4. The method according to claim 1, wherein prior to injection, the composition is fluid.

5. The method according to claim 1, wherein prior to injection, the microgel particle adopts a collapsed configuration.

6. The method according to claim 1, wherein prior to infection, the water content in the particle is less than about 30% (w/w) water.

7. The method according to claim 1, wherein prior to injection, the diameter of the microgel particle is between about 20-500 nm.

8. The method according to claim 1, wherein the pH of the tissue into which the microgel particle is infected is between about 6.0-7.5.

9. The method according to claim 1, wherein upon injection into the tissue, the diameter of the microgel particle increases or the microgel particles adopt a swollen configuration.

10. The method according to claim 9, wherein the microgel particles comprise at least about 95% (w/w) water when in the swollen configuration.

11. The method according to claim 9, wherein the average diameter of the microgel particles after injection increases by at least 200%.

12. The method according to claim 11, wherein the diameter of the microgel particles increases after injection to between about 200-400 nm.

13. The method according to claim 2, wherein the composition forms a gel in situ after injection into the tissue.

14. The method according to claim 10, wherein the particles in the swollen configuration comprise mobile ions.

15. The method according to claim 14, wherein the ions are $Na^+$ or $K^+$ ions.

16. The method according to claim 1, wherein the composition is prepared using free radical emulsion polymerisation.

17. The method according to claim 1, wherein the microgel particle comprises a polymer defined by the following formula I:

Poly(P-co-X) Formula I wherein, P is a pH-responsive co-monomer; and X is a functional cross-linking co-monomer.

18. The method according to claim 17, wherein the pH-responsive co-monomer is acidic.

19. The method according to claim 17, wherein the pH-responsive co-monomer comprises a substituted acrylic acid.

20. The method according to claim 17, wherein the pH-responsive co-monomer comprises methacrylic acid.

21. The method according to claim 17, wherein the functional cross-linking co-monomer comprises ethyleneglycol dimethacrylate or 1,4 butanediol diacrylate.

22. The method according to claim 1, wherein the microgel particle comprises a polymer defined by the following formula IV:

Poly(B-co-P-co-X) Formula IV wherein, P is a pH-responsive co-monomer; B is a hydrophobic co-monomer;

and X is a functional cross-linking co-monomer.

23. The method according to claim 22, wherein the hydrophobic co-monomer comprises methylmethacrylate or ethylacrylate.

24. The method according to claim 1, wherein the microgel particle comprises a polymer comprising: poly methylmethacrylate/methacrylic acid/ethyleneglycol dimethaacrylate (poly(MMA/MAA/EGDMa)) or poly ethylacrylate/methylmethacrylate/1,4-butanediol diacrylate (poly(EA/MAA/BDDA)).

25. The method according to claim 1, wherein the composition further comprises at least one nucleus pulposus cell, at least one stem cell, at least one mammalian cell, or a combination thereof.

26. The method according to claim 25, wherein the at least one mammalian cell comprises a chondrocyte.

27. The method according to claim 25, wherein the at least one stem cell comprises mesenchymal and/or haematopoeic stem cells.

28. The method according to claim 1, wherein the subject has damaged or degenerated load-bearing tissue.

29. The method according to claim 1, wherein the subject has a damaged or degenerated articular joint.

30. The method according to claim 1, wherein the subject has damaged or degenerated vertebral, or intervertebral discs (IVDs).

31. The method according to claim 1, wherein the subject has a condition selected from the group consisting of arthritis, intervertebral disc degeneration, back pain, low back pain, sciatica, cervical spondylosis, neck pain, kyphosis, scoliosis, degenerative joint disease, osteoarthritis, spondylolysis, spondylolisthesis, prolapsed intervertebral disc, failed spine surgery, and spinal instability.

* * * * *